(12) United States Patent
McCullen et al.

(10) Patent No.: US 9,393,097 B2
(45) Date of Patent: Jul. 19, 2016

(54) LAYERED FIBROUS CONSTRUCT

(75) Inventors: Seth Dylan McCullen, London (GB); Molly Morag Stevens, London (GB); Helen Autefage, London (GB)

(73) Assignees: Seth Dylan McCullen, London (GB); Molly Morag Stevens, London (GB); Helen Autefage, London (GB)

( * ) Notice: Subject to any disclaimer, the term of this patent is extended or adjusted under 35 U.S.C. 154(b) by 189 days.

(21) Appl. No.: 13/994,427

(22) PCT Filed: Dec. 16, 2011

(86) PCT No.: PCT/GB2011/001734
§ 371 (c)(1),
(2), (4) Date: Aug. 29, 2013

(87) PCT Pub. No.: WO2012/080706
PCT Pub. Date: Jun. 21, 2012

(65) Prior Publication Data
US 2013/0338791 A1 Dec. 19, 2013

(30) Foreign Application Priority Data
Dec. 16, 2010 (GB) .................................. 1021438.5

(51) Int. Cl.
*A61F 2/02* (2006.01)
*A61F 2/00* (2006.01)
(Continued)

(52) U.S. Cl.
CPC ................. *A61F 2/02* (2013.01); *A61F 2/0063* (2013.01); *A61L 27/38* (2013.01); *A61L 27/50* (2013.01); *A61L 27/58* (2013.01); *A61L 2430/06* (2013.01)

(58) Field of Classification Search
CPC . A61F 2002/4495; A61F 2/0063; A61F 2/04; A61F 2/08; A61F 2/10; A61F 2/12; A61F 2/24; A61F 2/28; A61F 2/44; A61F 2/02; A61F 2/30756; A61F 2002/30751; A61F 2002/30009; A61F 2002/30759; A61F 2/4618; A61L 27/38; A61L 27/50; A61L 27/58; A61L 2430/00; C12N 2533/30
USPC .................. 623/14.12, 17.11, 17.16, 23.72
See application file for complete search history.

(56) References Cited

U.S. PATENT DOCUMENTS

| 7,524,335 | B2 | 4/2009 | Slivka | |
|---|---|---|---|---|
| 2008/0112998 | A1 | 5/2008 | Wang | |
| 2013/0253663 | A1* | 9/2013 | Amoroso | ................ A61L 27/48 623/23.75 |

FOREIGN PATENT DOCUMENTS

| EP | 1537839 A1 | 6/2005 |
|---|---|---|
| EP | 1064958 B1 | 8/2005 |

(Continued)

OTHER PUBLICATIONS

Wise, Joel K., et al. 'Chondrogenic Differentiation of Human Mesenchymal Stem Cells on Oriented Nanofibrous Scaffolds: Engineering the Superficial Zone of Articular Cartilage'. 2009 Tissue Engineering. vol. 15, No. 4.

(Continued)

*Primary Examiner* — Jonathan W Miles
*Assistant Examiner* — George J Ulsh
(74) *Attorney, Agent, or Firm* — Lathrop & Gage LLP; Brian C. Trinque; Benjamin D. Heuberger

(57) ABSTRACT

The present invention relates to a layered fibrous construct for use as a scaffold for repairing or replacing cartilage or cartilage-like tissue, and a process for the production thereof.

33 Claims, 20 Drawing Sheets

(51) Int. Cl.
*A61L 27/38* (2006.01)
*A61L 27/50* (2006.01)
*A61L 27/58* (2006.01)

(56) References Cited

FOREIGN PATENT DOCUMENTS

| WO | WO 2005053578 A1 | 6/2005 |
| WO | WO 2006/113642 A1 | 10/2006 |
| WO | WO 98/53768 A2 | 9/2007 |
| WO | WO 2008098366 A1 | 8/2008 |
| WO | WO 2008100534 A2 * | 8/2008 ............. A61L 27/38 |

OTHER PUBLICATIONS

McCullen, Seth D., et al. 'In Situ Collagen Polymerization of Layered Cell-Seeded Electrospun Scaffolds for Bone Tissue Engineering Applications'. 2010 Tissue Engineering. vol. 16 No. 5.

Young Min Ju, et al. 'Bilayered Scaffold for Engineering Cellularized Blood Vessels'. 2010 Biomaterials 31. pp. 4313-4321.

International Search Report (WO2012080706) Dated Jul. 17, 2012.

* cited by examiner

2% agarose and Ø1 μm PCL fibres

Bilayer laminates of agarose, aligned, aligned-random, or random arrays were tested in shear.

SEQUENCE LISTING

```
<160> NUMBER OF SEQ ID NOS: 8

<210> SEQ ID NO 1
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer 1"
      /organism="artificial sequences"

<400> SEQUENCE: 1
accctcaaga ttgtcagcaa                                                   20

<210> SEQ ID NO 2
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
      /note="Primer 2"
      /organism="artificial sequences"

<400> SEQUENCE: 2
acgatgccaa agtggtca                                                     18

<210> SEQ ID NO 3
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
```

```
        /note="Primer 3"
        /organism="artificial sequences"

<400> SEQUENCE: 3
gctaccctga cccttcatc                                                    19

<210> SEQ ID NO 4
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
        /note="Primer 4"
        /organism="artificial sequences"

<400> SEQUENCE: 4
aagctttctg ggatgtccac                                                   20

<210> SEQ ID NO 5
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
        /note="Primer 5"
        /organism="artificial sequences"

<400> SEQUENCE: 5
cattaggggt cacaatggtc                                                   20

<210> SEQ ID NO 6
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
        /note="Primer 6"
        /organism="artificial sequences"

<400> SEQUENCE: 6
tggagttcca ttttcaccag                                                   20

<210> SEQ ID NO 7
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
        /note="Primer 7"
        /organism="artificial sequences"

<400> SEQUENCE: 7
catcccaccc tctcacagtt                                                   20

<210> SEQ ID NO 8
<211> LENGTH: 20
<212> TYPE: DNA
```

-continued

```
<213> ORGANISM: artificial sequences
<220> FEATURE:
<221> NAME/KEY: source
<222> LOCATION: 1..20
<223> OTHER INFORMATION: /mol_type="DNA"
      /note="Primer 8"
      /organism="artificial sequences"

<400> SEQUENCE: 8
gtctctgcct tgacccaaag                                              20
```

LAYERED FIBROUS CONSTRUCT

RELATED APPLICATIONS

This application is a 35 U.S.C. §371 filing of International Application No. PCT/GB2011/001734, filed Dec. 16, 2011, which claims priority to GB Patent Application No. 1021438.5, filed on Dec. 16, 2010. The entire contents of each of these documents are incorporated herein by reference in their entireties.

The present invention relates to a layered fibrous construct for use as a scaffold for repairing or replacing cartilage or cartilage-like tissue, and a process for the production thereof.

Articular cartilage is a highly organized, fibre-reinforced tissue that provides a low-friction and wear-resistant load bearing surface in diarthrodial joints. This tissue exhibits unique anisotropic mechanical properties and organization based on the density dependent and structural arrangement of its extracellular matrix components of proteoglycan molecules retained within a fibrillar type II collagen meshwork. This collagen meshwork provides the tensile reinforcing element of cartilage and is comprised of three main depth dependent zones which include the superficial, middle and deep zones. Within these zones, collagen fibres feature a varying alignment of parallel (superficial), random (middle), or perpendicular (deep) orientation with respect to the subchondral bone surface. As the fibre orientation varies throughout the depth of the tissue, the mechanical properties also vary in terms of zonal tensile strength and tensile modulus. Though articular cartilage can withstand approximately >$10^7$ loading cycles, it can undergo damage and degeneration due to abnormal or excessive loading eventually resulting in osteoarthritis. Intrinsic articular cartilage repair is limited due to the tissue's lack of blood supply, neural innervations, and low proliferative capacity of resident chondrogenic cells. Current treatments for articular cartilage repair include abrasion arthroplasty, microfracture, or implantation of autologous chondrocytes or bone-marrow-derived mesenchymal stem cells, and osteochondral autografts. However, the regenerated tissue suffers from limited integration with the surrounding cartilage, poor mechanical properties arising from the production of fibrocartilage versus hyaline cartilage, and lack of the zonal organization that is present within native cartilage. Zonal organization of cartilage is integral to the proper function of the tissue and current solutions are unable to regenerate this tissue's anisotropic mechanical properties (zonal tensile strength, zonal tensile modulus, bulk aggregate modulus), collagen fibre orientation, chemical gradients, and cellular distribution.

Accordingly, it is evident that a need exists for a construct which can be used as a scaffold to provide not only the mechanical integrity of native cartilage tissue, but also to assist with new extracellular matrix formation and organization.

The present invention provides a synthetic anisotropic, layered construct which exhibits zonal organisation and can be used to assist with cartilage formation. The invention also provides an electrospinning process for producing the construct. The construct mimics articular cartilage in terms of fibre organization and mechanical properties and is comprised of at least three distinctly different fibre layers in terms of i) fibre size (i.e. diameter of the fibre), ii) fibre organization or alignment, iii) fibre mechanics in terms of elongation, tensile modulus, and ultimate tensile strength. Specifically, this design is focused on exhibiting decreasing tensile strength, decreasing tensile modulus, with varying fibre organization. As well as exhibiting mechanical properties (compressive and tensile) suitable to provide mechanical integrity of native cartilage, the layered construct of the invention provides a scaffold through which chondrocytes or stem cells can penetrate and remain viable.

The first aspect of the invention therefore provides a layered construct for repairing or replacing cartilage or cartilage-like tissue, the construct comprising a first (superficial) layer, a second (middle) layer and a third (deep) layer, wherein the second layer is located between the first layer and the third layer, wherein:
  the first layer comprises polymeric fibres arranged in an orientation to provide anisotropic tensile properties, such that tensile strength of the first layer is greater in a direction substantially perpendicular to the direction of layering than in the direction of layering; and
  the second layer and the third layer comprise polymeric fibres wherein the polymeric fibres in at least one of the second layer and the third layer are randomly orientated.

In an embodiment of the invention, the polymeric fibres of the first layer are aligned polymeric fibres. Preferably, the fibres are aligned substantially perpendicular to the direction of layering. The polymeric fibres of at least one of the second layer and the third layer are randomly orientated and the polymeric fibres of the other of the second and the third layer are aligned or randomly orientated fibres.

In a preferred embodiment, the first layer comprises aligned polymeric fibres and the second and third layers comprise randomly-orientated polymeric fibres.

The construct is a synthetic construct for repairing or replacing cartilage or cartilage-like tissue. Preferably, the scaffold is for repairing or replacing articular cartilage.

In some embodiments of the invention, the average diameter of fibres within the third layer is greater than the average diameter of fibres within the second layer. Fibre diameter not only changes the tensile properties but also the physical properties such as pore size. In some embodiments, the average diameter of fibres within the third layer is greater than the average diameter of fibres within the second layer by a factor of 2 or more. Preferably the ratio of the average diameter size between the third layer and the second layer is from 10:1 to 3:1, more preferably from 6:1 to 4:1. In some embodiments, the average diameter of fibres within the first and second layers is equivalent.

In a preferred embodiment, the average diameter of fibres within the first, second and third layers are: first layer 0.1-5 µm; second layer: 0.1-5 µm; and third layer: 0.5-25 µm. In some embodiments, the average diameter of fibres within the first, second and third layers are: first layer 0.5-2 µm; second layer 0.5-2 µm; and third layer 3.5-6.5 µm.

The first layer of fibres has the strongest mechanical properties (tensile strength and/or tensile modulus) with respect to the second and third layers. Accordingly, in some embodiments of the construct of the invention, the second layer and the third layer each independently has a tensile modulus and/or tensile strength that is significantly lower (by a factor of 2 or more) compared to the tensile modulus and/or tensile strength of the first layer. The first layer preferably comprises aligned fibres. The second and third layers may be comprised of fibres that do not display fibre alignment within a single direction and have mechanical properties that are significantly weaker (by a factor of 2 or more) compared to the first layer.

The tensile strength of the first layer is the tensile strength observed when tensile force is applied in a direction substantially perpendicular to the direction of layering. The tensile modulus of the first layer is measured in the same direction as the tensile strength. If either of the second or third layers are anisotropic (for-example containing non-randomly orientated fibres), tensile measurements would also be taken in a direction substantially perpendicular to the direction of layering.

The tensile modulus of the third layer may be equivalent to, greater than or lower than the tensile modulus of the second layer. In a preferred embodiment, the tensile modulus of the third layer is lower than the tensile modulus of the second layer.

In certain embodiments, the tensile modulus of each layer is: first layer: 10-300 MPa; second layer: 3-100 MPa; and third layer: 0.5-20. In some embodiments, the tensile stress modulus of each layer is: first layer: 10-200 MPa; second layer: 3-20 MPa; and third layer: 0.5-20.

The tensile strength of the third layer may be equivalent to or lower than the tensile strength of the second layer. In a preferred embodiment, the tensile strength of the third layer is lower than the tensile strength of the second layer.

In certain embodiments, the tensile strength of each of the layers is: first layer: 10-200 MPa; second layer: 5-60 MPa; and third layer: 3-20 MPa.

In certain embodiments, the tensile strength of the construct is 5-30 MPa, for example 5-15 MPa.

In certain embodiments, the tensile modulus of the construct is 5-50 MPa, for example 5-40 MPa.

In some embodiments the compressive modulus of the construct, as measured in the direction of layering, is from 0.1-2 MPa.

In certain embodiments, the polymeric fibres of the first layer, second layer and third layer are each formed from a polymer which is preferably biocompatible and biodegradable. The first, second and third layers may be formed from the same polymer or different polymers, preferably from the same polymer. The polymer may be a synthetic polymer or a naturally occurring polymer. In certain embodiments the polymer is an aliphatic polyester. A suitable synthetic polymer may be a polymer selected from the group consisting of, but not limited to, poly(caprolactone), poly(lactic acid), poly (glycolic acid), poly(2-hydroxyethyl methacrylate), polydioxanone, poly(3-hydroxybutyrate), poly(3-hydroxyvalerate), poly(valcrolactone), poly(tartronic acid), poly(β-malonic acid), poly(propylene fumarate), polyanhydrides, tyrosine-derived polycarbonates, a polyorthoesters and olyphosphazenes. A suitable polymer may further be a polymer selected from the group consisting of, but not limited to, poly(glutamic acid), collagen, hyaluronic acid, fibrin, alginate, laminin, elastin, chitosan, silk, keratin, cellulose, collagen. Poly(glutamic acid) is preferably poly(gamma glutamic acid). Collagen is preferably type II collagen. The polymer of the invention may also be a copolymer, for example a copolymer of any of the polymers mentioned above. The polymeric fibres may also be formed from a mixture of any of the polymers mentioned above. Preferred polymers include poly(caprolactone), poly(lactic acid) and poly(gamma glutamic acid).

In some embodiments wherein the polymeric fibres comprise, for example, poly(caprolactone), the tensile strength of each of the layers may: first layer: 30-40 MPa; second layer: 5-10 MPa; and third layer: 2-10 MPa; and the tensile modulus of each of the layers may be: first layer: 60-90 MPa; second layer: 7-15 MPa; and third layer: 5-10 MPa. The tensile strength of the construct may be 5-30 MPa and the tensile modulus of the construct may be 5-40 MPa.

The polymer used to form the polymeric fibres is provided at a molecular weight suitable for fibre formation for linear polymer chains. In some embodiments the molecular weight ($M_w$) is from 10,000 to 2,000,000 Da. Preferably, the $M_w$ is at least 60,000. In some embodiments, the $M_w$ is from 10,000 to 600,000 Daltons, preferably 60,000 to 180,000 Daltons.

In certain embodiments, the construct comprises one or more additional layers. For example, in certain preferred embodiments the construct comprises a base layer adjacent the third (deep) layer. In some embodiments the base layer comprises an inorganic material, for example selected from the group consisting of a calcium phosphate material and/or a bioactive glass. The base layer may comprise a composite material comprising polymeric material (such as polymeric fibres as defined for any of the first, second and third layers) and an inorganic material. The base layer may, for example, comprise polymeric material with inorganic material coated thereon or dispersed therein.

In certain embodiments, the construct further comprises an additional component integrated within one or more of the first, second and third layers. The additional component can be selected from the group consisting of, but not limited to, decellularized xenogenic or allogenic tissue components, a growth factor, a protein or peptide, a hydrogel, a carbohydrate, an inorganic bioactive compound such as a bioactive glass or calcium phosphate crystals. In some embodiments the protein or peptide is a protein or peptide selected from the group consisting of, but not limited to, a collagen (such as type II collagen), a collagen mimicking protein or peptide (such as a type II collagen mimicking protein or peptide), fibronectin, a globular protein (such as serum albumin), a proteoglycan, and a fibrous protein or peptide. Functionalisation of the construct with an additional component can provide beneficial properties, for example tailoring of hydrophobicity, and these properties can promote cellular adhesion to the construct. As an example, functionalization of a polycaprolactone construct with collagen increases the hydrophobicity of the construct which has been shown to be beneficial for cellular adhesion. In addition, functionalisation of the construct with a protein recognised by cells (such as collagen) can act to promote cellular adhesion. Hydrogel materials can be incorporated into the construct as a delivery vehicle to assist with cellular seeding, to incorporate bioactive molecules, or to increase mechanics of the scaffold. Hydrogel materials can range from natural biopolymers including fibroin, hyaluronan, collagen, etc., synthetic materials including polyethylene glycol, synthetic peptide materials, and any combination thereof.

In some embodiments, the construct is seeded with cells. The cells can be selected from the group consisting of, but not limited to, chondrocytes, chondroprogenitors, mesenchymal stem cells (obtained from bone marrow or adipose tissue), fibroblasts, fibrochondrocytes, and osteoblasts.

In some embodiments the first, second and third layers of the construct are formed by sequential electrospinning and therefore comprise a single entity without any additional joining layers between the first, second and third layers. In alternative embodiments the first, second and third layers are formed separately by electrospinning and then assembled into a single construct by solvent bonding utilising a hydrogel polymer solution.

In a construct of the invention, the second and third layers will have some porosity as a result of the random orientation of the fibres forming these layers. Porosity is beneficial for the ability of seeded cells to infiltrate the construct and is also able to assist with mass transfer.

In some embodiments of the invention, the thickness of the construct can vary between 0.5-3 mm. The thickness of the construct is the thickness in the direction of layering. This can be patient specific. In some embodiments, the specific thicknesses of each layer, in terms of proportion of the overall thickness of the construct, are approximately the following:
first layer (superficial layer): 10-30%;
second layer (middle layer): 20-40%;
third layer (deep layer): 30-70%.

It will be appreciated that the features and embodiments described for the first aspect of the invention can be present in combination in a construct of the invention.

In a second aspect, the invention provides a process of producing a layered construct, the process comprising:
a) electrospinning a polymer to form a first (superficial) layer of polymer fibres,
b) electrospinning a polymer to form a second (middle) layer of polymer fibres, and
c) electrospinning a polymer to form a third (deep) layer of polymer fibres, wherein the construct is assembled to have the second layer positioned
between the first layer and the third layer, wherein the first layer comprises polymeric fibres arranged in an orientation to provide anisotropic tensile properties, such that tensile strength of the first layer is greater in a direction substantially perpendicular to the direction of layering than in the direction of layering, and wherein the second layer and the third layer comprise polymeric fibres wherein the polymeric fibres in at least one of the second layer and the third layer are randomly orientated.

In a preferred embodiment, the electrospinning parameters are chosen such that the layers have one or more of the following properties:
i) the average diameter of fibres within the third layer is greater than the average diameter of fibres within the second layer;
ii) the second layer and the third layer have a tensile modulus and/or tensile strength that is significantly lower (by a factor of 2 or more) compared to the first layer.

In some embodiments of the invention the process is a solvent electrospinning process in which a first polymer solution, second polymer solution and third polymer solution are electrospun to produce the first, second and third layers, respectively. In alternative embodiments, the process is a melt-electrospinning process, where the polymer is heated above its melting temperature ($T_m$) and electrospun in a molten state.

In certain embodiments, the first, second and third polymer solutions each comprise polymer solubilised in a solvent or solvent mixture. The solvent or solvent mixture may be a chlorinated solvent such as dichloromethane or chloroform, methylene chloride, dimethyl formamide (DMF), tetrahydrofuran, acetone, 1,1,1,3,3,3 hexa-fluoro isopropanol (HFIP), or a mixture thereof. In some embodiments, the solvent is a chloroform/DMF mixture (preferably 3:1) or HFIP.

The concentration of the polymer solutions can be used to tailor the fibre diameter of fibres produced, with an increase in polymer concentration resulting in an increase in fibre diameter. Fibre diameter can also be modified depending on the molecular weight of the polymer that is used. An increase in molecular weight will result in an increase in fibre diameter. Fibre diameter can also be modified by tailoring volumetric flow rate, electric field settings, and/or gauge of the needle used in the electrospinning process. Accordingly, it will be appreciated that a wide range of concentrations of the first, second and third polymer solutions, for example within the range of 1%-70% w/v, may be used in the process of the invention. In some embodiments, the concentration of polymer in the third polymer solution is greater than the concentration of polymer in the second solution. As an example, in some embodiments, the concentration of polymer in the first and second polymer solution may be in the range of 10-20% w/v and, in some embodiments, the concentration of polymer in the third polymer solution is 20-30% w/v. In alternative embodiments the concentration of the third polymer solution is not greater than the concentration of the second polymer solution.

The polymer is preferably a polymer as defined in respect of the first aspect of the invention.

In some embodiments the first, second and/or third polymer solutions comprise an additional component selected from the group consisting of, but not limited to, decellularized xenogenic or allogenic tissue components, a growth factor, a protein or peptide, a hydrogel, an inorganic bioactive compound such as a bioactive glass or calcium phosphate crystals. In some embodiments the protein or peptide is a protein or peptide selected from the group consisting of, but not limited to, a collagen (such as type II collagen), a collagen mimicking protein or peptide (such as a type II collagen mimicking protein or peptide), fibronectin, a globular protein, a proteoglycan, and a fibrous protein or peptide.

In preferred embodiments of the process of the invention, the first, second and third polymer layers are electrospun onto a rotating collector. The speed of rotation of the collector is determined to provide necessary fibre alignment. Accordingly, the collection speed (i.e. speed of rotation of the collector) for the first layer is greater than the collection speed for the second and third layer, such that aligned fibres are collected for the first layer and randomly oriented fibres are collected for the second and third layers. The collection speed for the first layer is at least 1000 rpm, preferably at least 1500 rpm. Preferably, the collection speed for the second and third layers is from 10-500 rpm, preferably 10-100 rpm.

In another embodiment, a static plate collector is used to collect the second and/or third layers.

In yet another embodiment, the first layer can be electrospun to form an aligned fibre layer using a static parallel bar collector, wherein fibres are collected between the two bars.

The process of the second aspect of the invention, in certain embodiments, is a sequential process comprising sequentially electrospinning the first, second and third layers onto the same rotating collector to produce a layered construct.

In alternative embodiments, the process of the invention comprises separately electrospinning each of the first, second and third layers and then laminating the layers together with a hydrogel to form a layered construct. Any hydrogel material can be used. Preferably the hydrogel is an agarose gel, fibrin glue, alginate, hyaluronic acid, polyethylene glycol or type I collagen. An exemplary hydrogel that can be used is 2% agarose gel.

An advantage of embodiments of the process where the first, second and third layers are spun separately is that the process allows facile post-processing to be carried out in a layer dependent manner. For example, the process may comprises tailored micromachining of individual layers to generate macropores that can be varied in size from 10-1000 µm. Such micromachined features can promote cell patterning, assist with mass transport, laminate integration and cell infiltration. Micromachining can be carried out by laser ablation.

Laser ablation or micromachining can also be used carried out on the layered construct as produced either by sequential electrospinning or lamination of separately produced layers. This can improve mass transport and porosity with minimal loss of mechanical properties.

In an additional embodiment of the invention, the process comprising any of the features described above further comprises the step of functionalising the layered construct with by exposure of the construct to a protein or peptide. This causes attachment of the protein to the construct, for example by physical adsorption or chemical grafting. In some embodiments the protein or peptide is a protein or peptide selected from the group consisting of, but not limited to, a collagen (such as type II collagen), a collagen mimicking protein or peptide (such as a type II collagen mimicking protein or peptide), fibronectin, a globular protein (such as a serum albumin), a proteoglycan, and a fibrous protein or peptide. The protein or peptide may be provided for the functionalisation step in phosphate buffered saline or acidic conditions of hydrochloric acid or acetic acid (dilute acidic conditions). In a specific embodiment, the construct is functionalised by exposure to a solution type II collagen. Preferably, the construct is treated with type II collagen at a concentration of 10 μg/ml for 12 hrs. In an additional embodiment of the invention, the process comprising any of the features described above further may comprise the step of functionalising the layered construct with by exposure of the construct to a hydrogel (e.g. as described above in respect of the first or second aspects of the invention).

Features and embodiments as described for the first aspect of the invention apply mutatis mutandis to the second aspect of the invention.

In a third aspect, the invention provides a construct as produced by the process of the second aspect of the invention.

In a fourth aspect, the invention provides a method of repairing, replacing or promoting regeneration of cartilage or cartilage-like tissue, the method comprising implanting a construct of the first aspect of the invention or a construct as produced by the process of the second aspect of the invention into an implantation site in a subject in need of repair, replacement or regeneration of cartilage or cartilage-like tissue. In certain embodiments the method is a method of repairing, replacing or promoting regeneration of articular cartilage. The site of implantation may be a site where there is damage or degeneration of cartilage (e.g. articular cartilage) or cartilage-like tissue.

In a fifth aspect the invention provides a construct of the first aspect of the invention for use in repairing, replacing or regenerating cartilage or cartilage-like tissue In a sixth aspect, the present invention provides a device comprising a construct of the first aspect of the invention. The device may be a cartilage scaffold or an osteochondral plug.

Preferred features of the first and second aspects of the invention apply mutatis mutandis to the third, fourth, fifth and sixth aspects of the invention.

The invention may be put into practice in various ways and a number of specific embodiments will be described by way of example to illustrate the invention with reference to the accompanying figures, in which:

FIGS. 1A-1D show small angle light scattering patterns and resulting vector maps and angular distributions for electrospun fibres with a random fibre orientation or aligned fibre orientation, collected onto a rotating mandrel at either 20 rpm or 1800 rpm, respectively. FIG. 1A shows the small angle light scattering pattern of highly aligned electrospun fibres and resulting vector map and orientation of electrospun materials. FIG. 1B shows the small angle light scattering pattern of randomly oriented electrospun fibres and resulting vector map and orientation of electrospun materials. FIGS. 1C-D show the fibre orientation-representing angular distributions of electrospun fibres, illustrating the distinction between randomly oriented (C) and highly aligned (D) fibres.

Figure 9:
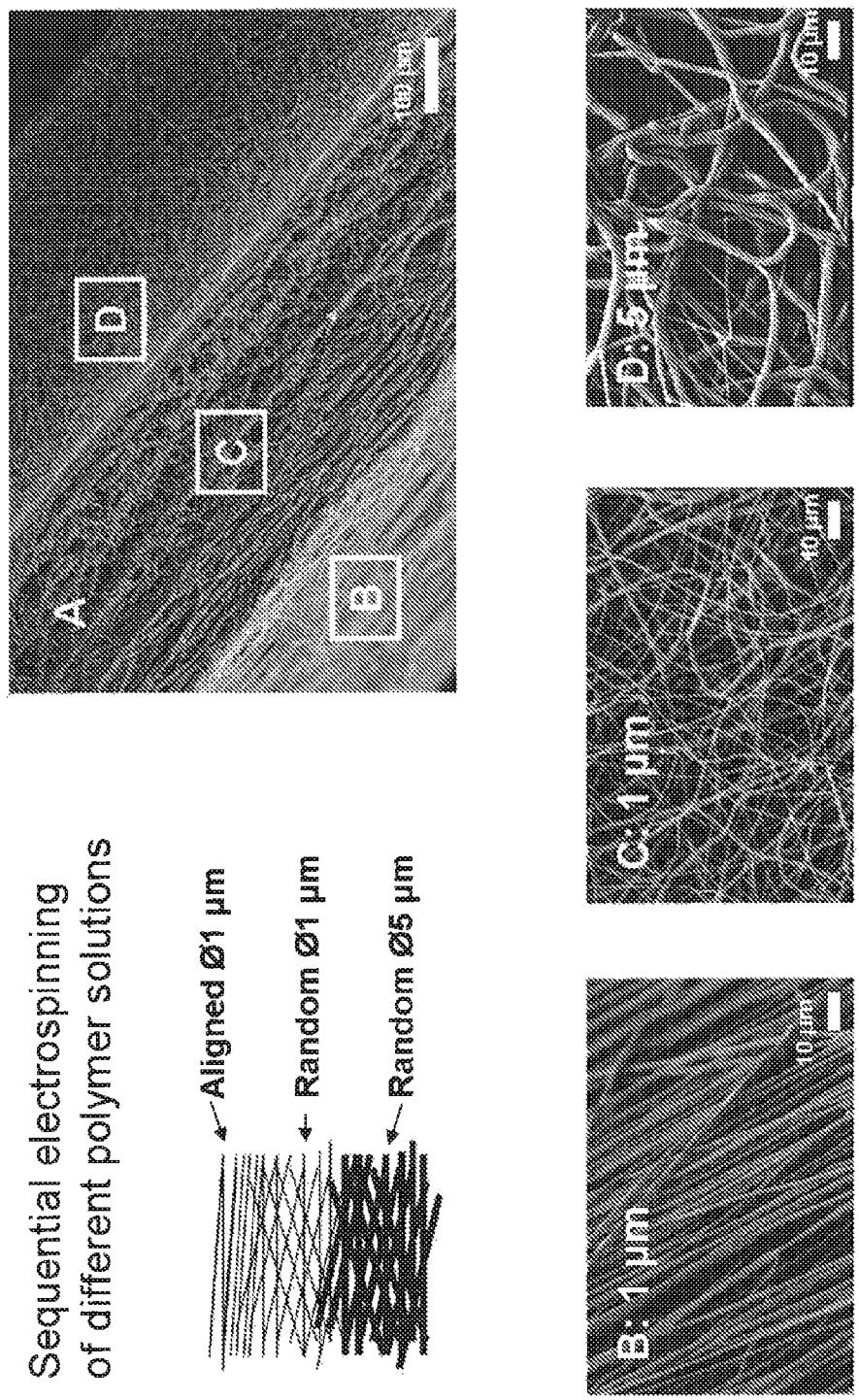

FIG. 9 shows a representation and electron microscopy images of the bulk construct (A) and the varying fibres of either aligned 1 μm (B), random 1 μm, or random 5 μm fibres throughout the construct.

Figure 10:
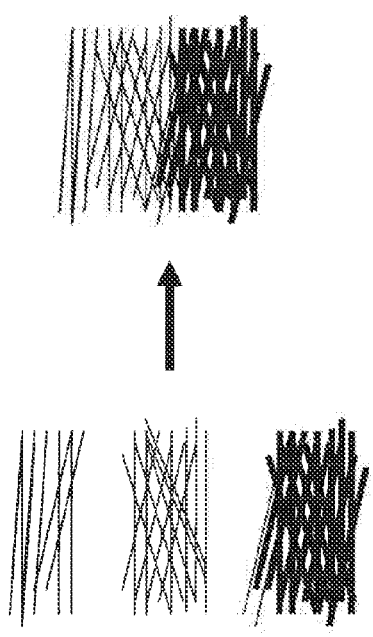
Figure 10:
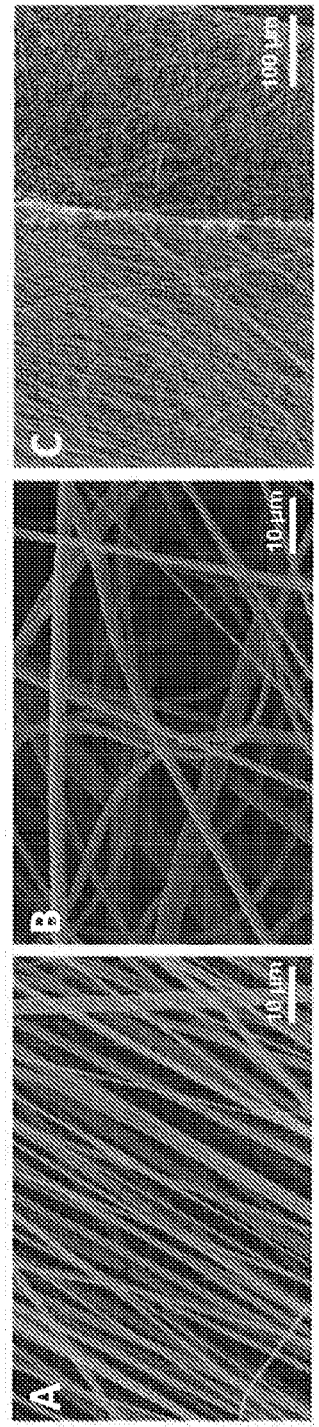

FIG. 10 shows a diagram of post assembly and lamination of electrospun scaffolds and accompanying electron micrographs of aligned (A), random (B), and the laminated scaffolds (C).

Figure 11:
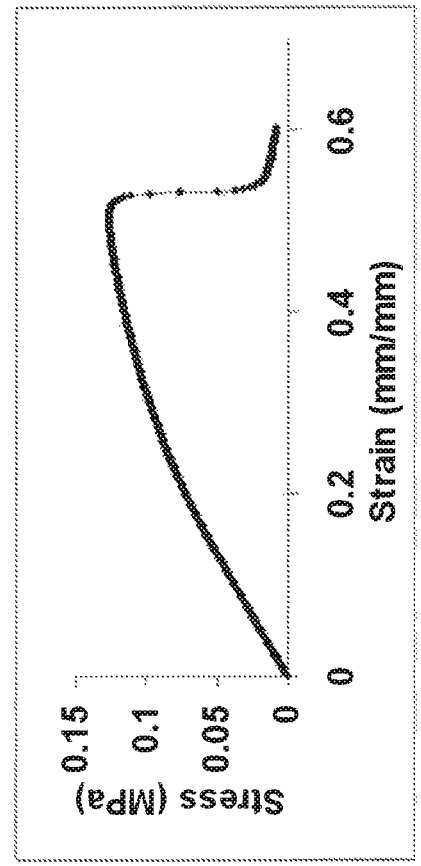
Figure 11:
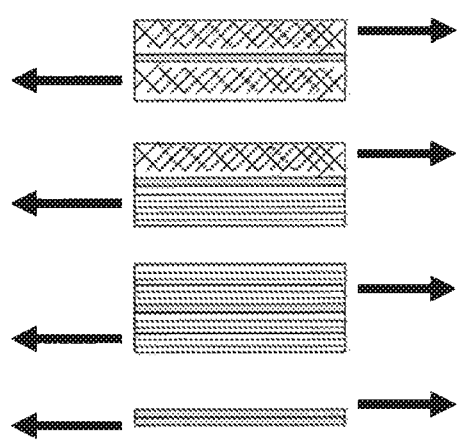

FIG. 11 shows a representation of pure agarose sheets, or laminated electrospun scaffolds of varying fibre combinations of aligned/aligned, aligned/random, or random/random scaffolds and the results of interfacial testing these in lap shear mode to determine the interfacial strength and the stiffness of the integrated scaffolds. The stress/strain curve is illustrated for the random/random scaffold.

Figure 12:
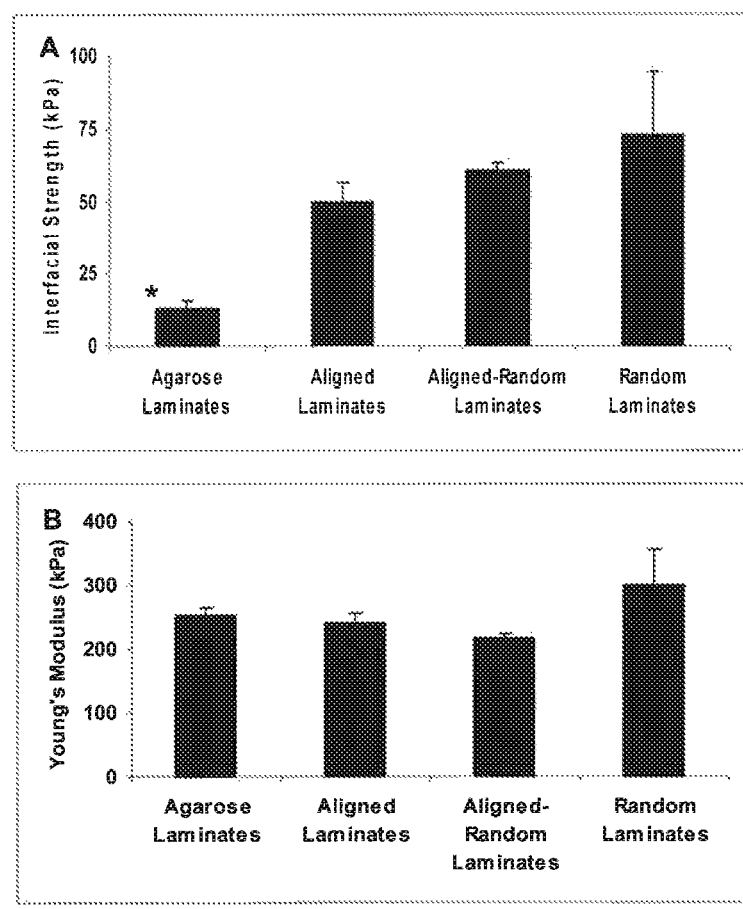

FIG. 12 shows plots of interfacial strength (kPa) and Young's modulus (kPa) for agarose laminates, aligned laminates, aligned-random laminates and random laminates as illustrated in FIG. 11. Fibre laminates significantly increased the interfacial strength compared to agarose laminates (A), yet the modulus of the laminate integration was unaffected by the addition of electrospun scaffolds (B).

Figure 13:
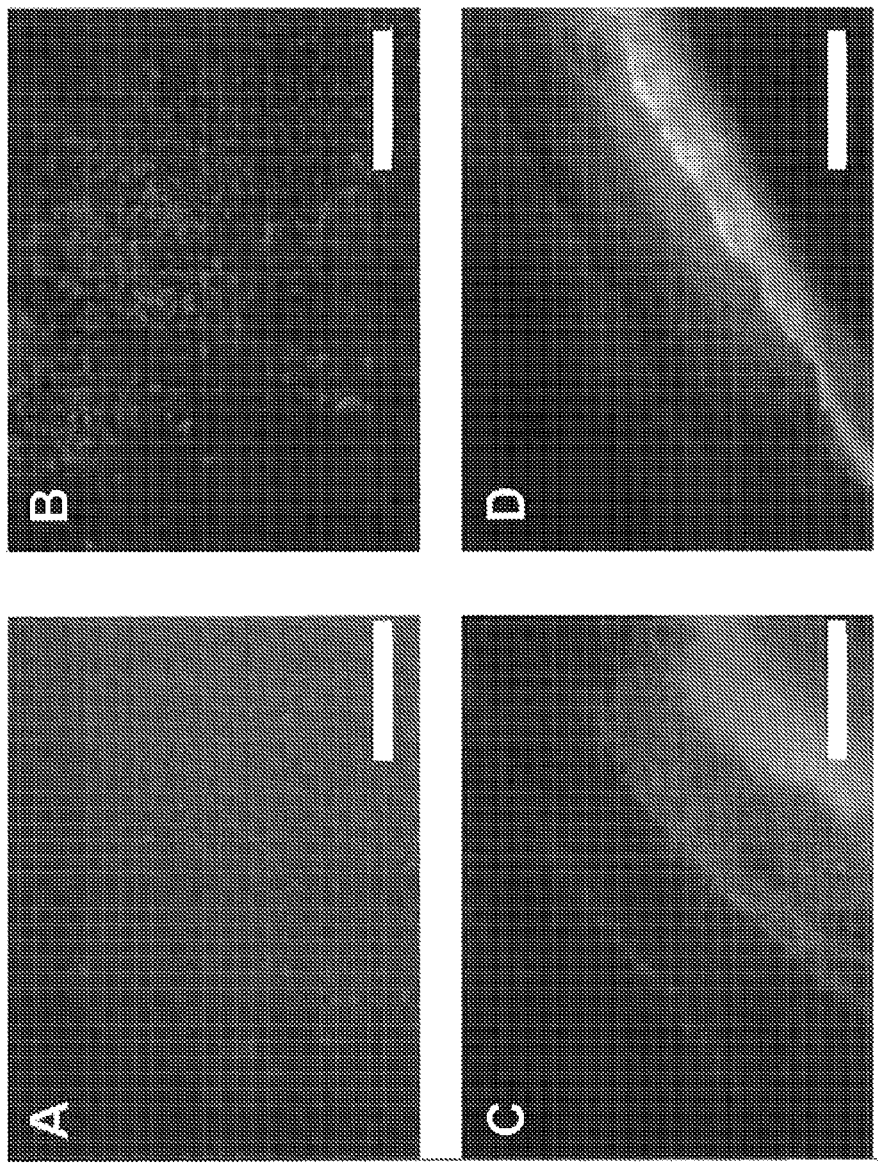

FIG. 13 shows chondrocyte viability on sequential electrospun constructs showing cellular viability and the aligned (A) and random (B) surfaces and cellular migration into the construct (C-D). Scale bar=200 μm in A-C and 500 μm in D.

Figure 14:
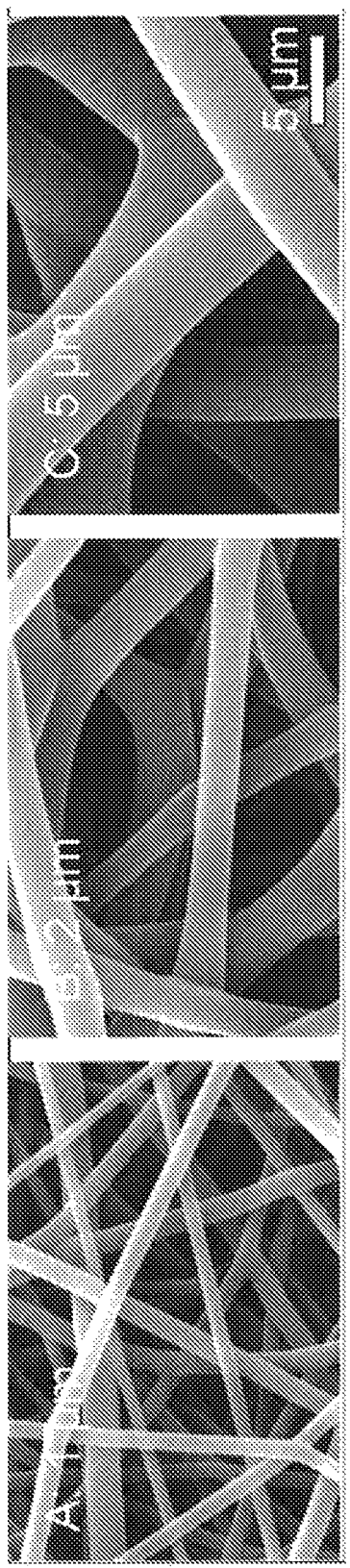

FIG. 14 shows electrospun PLA fibres (randomly orientated) at varying fibre diameter of either 1, 2, or 5 μm.

Figure 15:
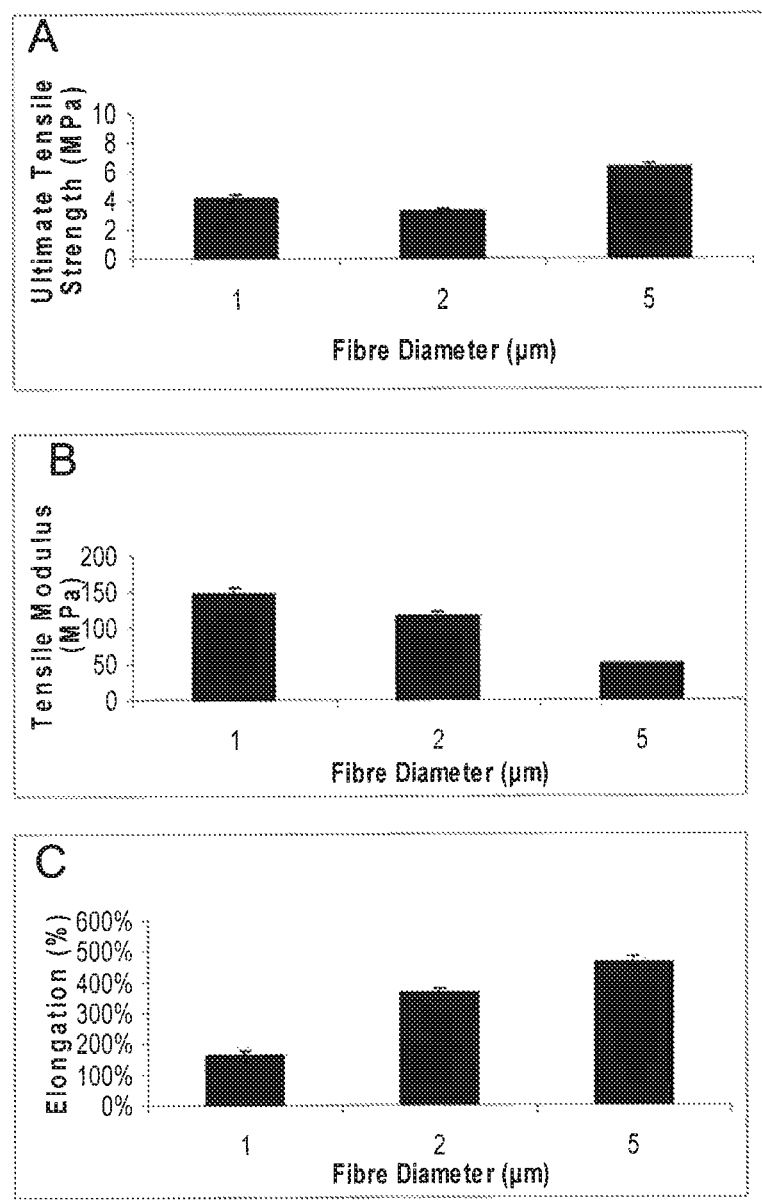

FIG. 15 shows plots of mechanical properties of electrospun PLA (randomly orientated) of ultimate tensile strength (A), tensile modulus (B), or elongation (C).

Figure 16:
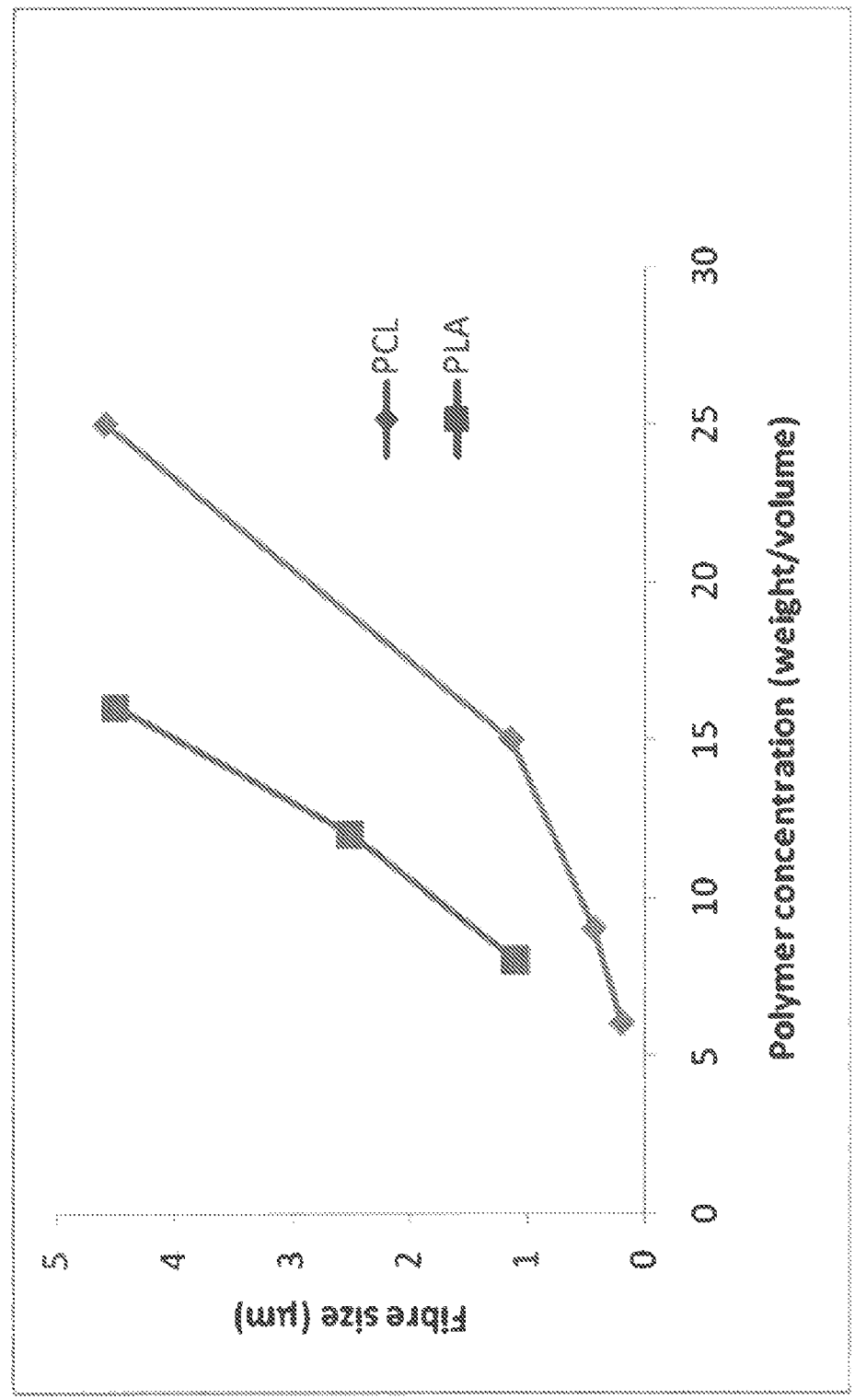

FIG. 16 shows a plot of fibre size as a function of polymer concentration for PLA and PCL, demonstrating that fibre size for both polymers increases respective to polymer concentration.

Figure 17:
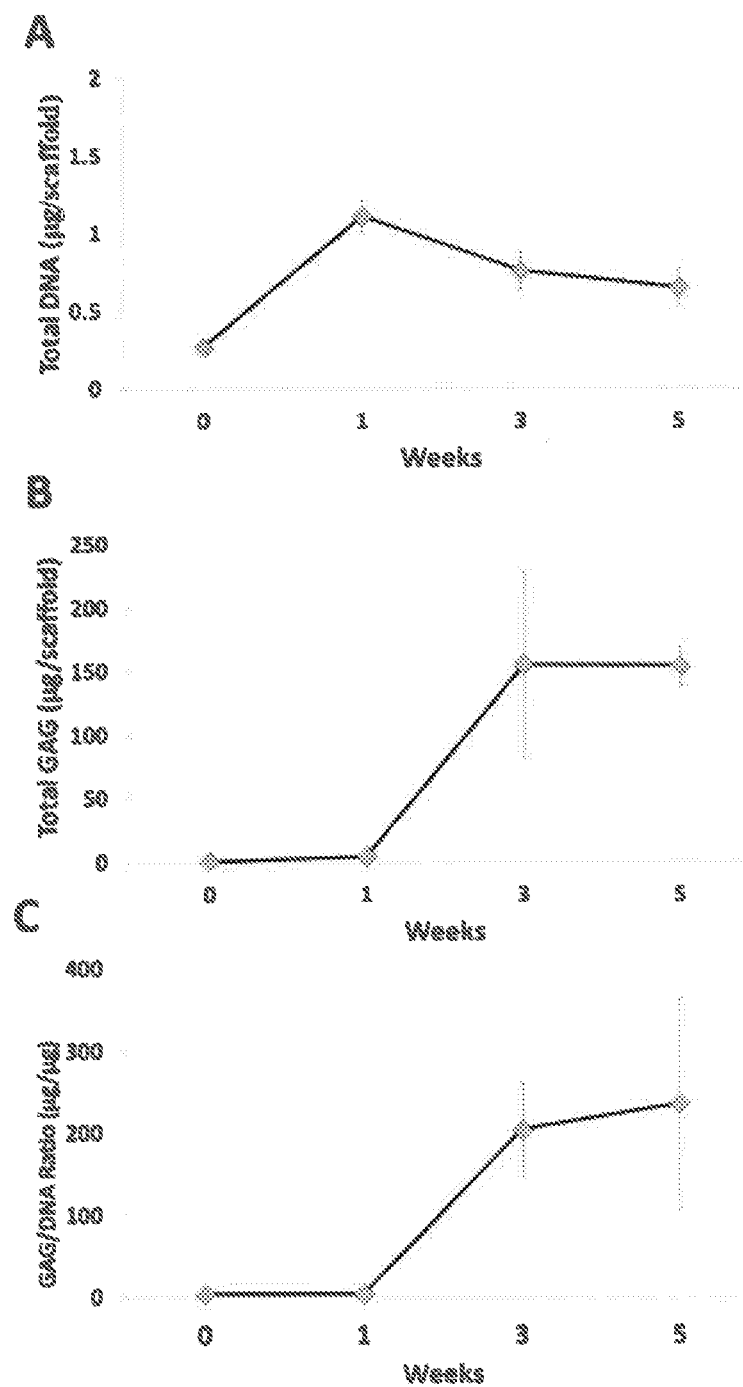

FIG. 17 shows DNA and GAG content in chondrocyte-seeded scaffolds during a 5 week culture period.

In the context of this invention fibres of a layer are considered to be "aligned" if the bulk fibres of a layer are substantially parallel to each other, i.e. the bulk fibres of a layer have a low angular variation with respect to a single direction. A layer is considered in the context of this invention to comprise aligned fibres if the bulk content of fibres with the layer exhibits and angular variation of no more than ±300 with respect to a single direction. Preferably, the angular variation is no more than ±20° with respect to a single direction. Fibre alignment can be analyzed using a digital image processing technique using small angle light scattering patterns. In the context of this invention, small angle light patterns were generated from a Helium Neon laser ($\lambda$=632.8 nm @ 5 mW). Aligned fibres scatter light perpendicular to their respective alignment while randomly orientated fibres do not display a preferred orientation. This image-processing technique can be used in estimating local directionality and angular variation. All images used in the process were obtained using an Olympus image system (CK-40 with C-5050; Olympus, Japan) at a resolution of 640×480 pixels. The analysis of each image yielded a distribution of fibre orientations, fibre alignment was quantified using custom algorithm implemented using MATLAB (ver. 6.0, Mathworks Inc., Natick, Mass., USA).

The 'bulk fibres of a layer' refers to substantially all of the polymeric fibres forming a layer, i.e. at least 90% (by volume), preferably approximately 100%.

The first layer of the construct of the invention exhibits anisotropic tensile properties. In preferred embodiments of the invention these anisotropic properties are as a result of the fibre alignment within the layer.

In the context of this invention fibres of a layer are considered to be "randomly orientated" if the bulk fibres of a layer do not display any significant alignment with respect to any single direction. The bulk fibres of a randomly orientated layer do not show an angular variation of lower than ±30° with respect to any single direction.

A 'biodegradeable' polymer in the context of this invention is a polymer that is degradeable within the body. Polymer degradation can be based on hydrolytic degradation or enzymatic degradation.

The polymer used to form the polymeric fibres making up the construct of the invention is of a molecular weight suitable for fibre formation. The molecular weight $M_w$ of the polymer is preferably from 10,000 to 2,000,000 Da. Preferably, the $M_w$ is at least 60,000. In some embodiments, the $M_w$ of the polymer is from 10,000 to 600,000, or from 60,000 to 180,000. Molecular weight $M_w$ (weight average molecular weight) can be determined using size exclusion or gel permeation chromatography.

A 'layered' construct is a construct comprising two or more layers having distinguishable compositions and/or physical properties. Processes for forming a layered construct include sequential electrospinning of a multiple polymer solutions onto the same collector or forming separately produced layers which are adhered together to give a layered structure. Although a layered construct will always have layers that are distinguishable in terms of their composition and/or properties, the layers do not necessarily need to be formed separately. Thus, layers could also be considered to be 'zones'. The constructs of the invention comprise at least three distinguishable layers. A layered construct has a direction of layering, which is the direction equally extending through the first, second and third layers. This is represented by the dotted line extending through the first, second and third layers shown in FIGS. 9 and 10. The direction of layering also corresponds to the axis of insertion for the construct of the invention.

Where a direction is referred to as being 'substantially perpendicular' to another direction, a variation of ±20°, preferably ±10°, more preferably +5° from a direction perpendicular to the other direction is allowed.

The 'tensile strength' of a material can also be referred to as the 'ultimate tensile strength'. Tensile strength is also known as tensile stress and within the context of this application 'tensile strength' and 'tensile stress' are used interchangeably. The tensile strength of a material is the maximum stress that a material can withstand while being stretched or pulled before necking. As is well know in the art, tensile strength can be measured by performing a tensile test and recording the stress versus strain, with the highest point of the stress-strain curve being the tensile strength. For an isotropic layer (such as a layer of randomly-orientated fibres) tensile strength will be equivalent in any direction. For an anisotropic layer (or anisotropic/layered construct), tensile measurements are carried out in a direction substantially perpendicular to the direction of layering.

The 'tensile modulus' describes the tensile elasticity and corresponds to the ratio of tensile stress to tensile strain. For an anisotropic layer (or construct), the tensile modulus is measured in the same direction as the tensile strength. In the context used herein, tensile modulus may also be referred to as Young's modulus.

Tensile measurements can be performed on layers prior to construction into a layered construct, or on layers representing the polymer composition of a layer within a layered construct. Tensile measurements can also be performed on a construct (as a whole).

An 'anisotropic' material is a material having properties that differ according to the direction of measurement. The first layer of the construct of the invention is anisotropic due to the arrangement of fibres. Where the tensile strength of this layer is referred to in the context of the invention, the tensile strength is the tensile strength value observed where tensile force is applied substantially perpendicular to the direction of layering. In preferred embodiments this corresponds to the direction of orientation of the fibres.

A 'bioactive' material is a material which actively participates within the regeneration/healing process by directing cellular processes.

The construct of the invention is useful for the repair, replacement and regeneration of cartilage and cartilage-like tissue. Cartilage-like tissue can be defined as dense connective tissue comprised of proteoglycan and collagen.

The construct of the invention comprises polymeric fibres. The diameter of these fibres can be measured using imaging software. For example, fibres diameters referenced herein were measured using the software program Image J (National Institutes of Health, Bethesda, Md., USA) and the fibre diameters are reported as average±standard error mean. Accordingly, when fibre diameters are referred to herein they are an average fibre diameter±standard error mean.

In some embodiments of the invention, the construct is produced by sequential electrospinning of multiple polymer solutions onto the same collector. A construct fabricated using sequential electrospinning will comprise a single entity with multiple layers of differing fibre size, fibre orientation and fibre mechanics. In other embodiments of the invention, the construct is produced by separately fabricating individual layers of electrospun polymeric fibres, with varying fibre size, orientation and mechanics and assembling the individual layers into a single construct via solvent bonding by utilizing a low concentration polymer solution (1-4% weight/volume).

Electrospun fibrous scaffolds with diameters on the micron to submicron size scale can be used as scaffolding for articular cartilage regeneration, as these materials are able to mimic natural cell-extracellular matrix interactions, promote production of cartilage-like tissue, and provide a template to organize the newly deposited matrix. Electrospinning is a facile technique to generate dense fibre networks that are capable of providing a compliant, biocompatible matrix, and offers tunable physical properties in terms of fibre size, spacing, and orientation. Electrospinning is a process which uses electrostatic interactions between a polymer solution and an extremely high electric potential to draw fibres from a polymer solution. Standard electrospinning apparatus comprises a spinneret (generally a hypodermic syringe needle) connected to a high-voltage (5-50 kV) direct current power supply, and a collector. Electrospinning must generate high shear to induce initial fibre formation by overcoming the impeding surface tension of the polymer solution. Once the surface tension is overcome a polymer jet erupts from the spinneret forming a stable region known as the Taylor cone that then undergoes significant elongation during the rapid whipping instability. As the polymer jet travels from the electrified tip to the collector fibre solidification occurs as solvent evaporates, forming fibrous materials. Fibres of varying diameters can be created by altering either solution conditions and/or external operational conditions. Fibre diameter plays a critical parameter in terms of mechanical properties and the physical properties of the bulk scaffold. By varying fibre diameter (fibre size) the resulting fibre networks can have significantly different properties in terms of physical properties such as pore size and mechanical strength. Moreover, the size scale of the fibres can dictate cellular behaviour, as fibres with diameters less than 0.5 µm have been shown to promote cell spreading, proliferation, and matrix production (sulfated glycosaminoglycan content) of chondrocytes.

In addition to varying fibre size, fibre orientation can be varied through use of different collector geometries or by varying the rotation (collection) speed of a rotating collector. Aligned electrospun scaffolds are known to exhibit significant increases in strength, modulus, and also able to guide extracellular matrix formation along the axis of the fibre direction. However, aligned electrospun scaffolds have not been incorporated into a larger bulk structures that resemble the trilaminar design of articular cartilage. In this work we investigate the effect of fibre size on the bulk material properties of biocompatible biodegradable electrospun laminates of poly(ε-caprolactone) and examine the effect of fibre size on in vitro cell adhesion and chondrogenesis of human chondrocytes. Finally we show that by varying both fibre size and orientation, we can create an anisotropic scaffold that mimics both the fibre organization and more importantly the zonal tensile properties of articular cartilage.

By varying fibre diameter of electrospun scaffolds, materials with significantly different bulk mechanical properties can be fabricated. Though the fibrous scaffolds can have a range of fibre diameters from 0.2-25 µm, we have determined that there is little effect on the biochemical content of these materials after being seeded with human chondrocytes for up to 35 days. This data indicates that fibre size does not significantly affect chondrogenesis, or more importantly, electrospun fibres greater than 0.5 µm, specifically 1 and 5 µm, do not impede chondrogenesis in vitro.

To create a trilaminar, anisotropic scaffold with varying fibre orientations and mechanical properties, sequential electrospinning can be performed by depositing polymer solutions under varying collection conditions (i.e. varying collector speed) and by varying polymer solution concentration onto the same collector. Lamination of individual scaffolds can be achieved to create the trilaminar scaffolds by bonding individual scaffolds with a biocompatible gel such as agarose. The addition of the fibre scaffolds significantly increases the interfacial strength between the individual scaffolds but does not improve the stiffness of the interface, as this is largely dominated by the gel itself. This work demonstrates a proof of principle for creating anisotropic trilaminar fibrous scaffolds that are able to mimic the zonal fibre organization, compressive and mechanical properties of articular cartilage.

Additional components can be incorporated into one or more of the first, second and third layers of the construct of the invention to provide the construct with additional advantageous properties. These components may be incorporated within the first, second and or first polymer solution from which the layers are created by electrospinning. For example, decellularized extracts from cartilage tissue can be incorporated by a process in which articular cartilage is excised from a bovine knee, pulverised to form a slurry, digested with detergent (e.g. 0.5-2% SDS or sodium deoxycholate with protease inhibitors) and treated with bovine DNAse type I that has been activated with magnesium and calcium, to degrade cellular DNA. Following decellularization and DNAse treatment the tissue slurry can be heated to inactive DNAse (e.g. at 60° C. for 10 mins), washed with deionized water, filtered (e.g. with a 50 micron pore diameter nylon filter), frozen and lyophilized (e.g. at −98° C. for 12 hours). Such a process produces a homogenous cartilage powder that can be blended with the first, second or third polymer solutions.

The invention will now be illustrated by reference to the following non-limiting examples.

EXAMPLE 1

Scaffold Fabrication with Varying Fibre Diameters:

Electrospun scaffolds were fabricated by electrospinning poly(ε-caprolactone) (PCL) with a $M_n$ of 80,000 Da that was dissolved in either 1,1,1,3,3,3-hexafluoroisopropanol (HFIP) or a 3:1 mixture of chloroform/dimethyl formamide (all reagents from Sigma Aldrich) at either 6, 9, 15, or 25% w/v and electrospun at optimal operational conditions to generate randomly oriented fibre scaffolds with distinct fibre sizes as reported in Table 1.

TABLE 1

Electrospinning parameters for generating varying fibre diameters from PCL.

| Solution | Target fibre diameter (µm) | Solvent | PCL (wt/v %) | Flow rate (mL/hr) | Voltage (kV) | Collection Distance (cm) | Needle |
|---|---|---|---|---|---|---|---|
| A | 0.2 | HFIP | 6 | 3 | 20 | 10 | 25G |
| B | 0.35 | 3:1 Chloroform/DMF | 9 | 3 | 15 | 14 | 27G |
| C | 1 | HFIP | 15 | | 15 | 10 | 16G |
| D | 5 | 3:1 Chloroform/DMF | 25 | 3 | 15 | 14 | 16G |

The various parameters of the electrospinning process affect the diameter of the fibre produced. PCL with a $M_n$ of 80,000 was chosen because it is commercially available in large quantities from an international supplier. The molecular weight of the polymer can vary significantly and is based on achieving sufficient polymer chain entanglements to allow fibre formation to occur. The rationale between the choice of particular solvents is that the polymer must be soluble in the chosen solvent and not clog the nozzle or the syringe needle. Other solvents include dichloromethane, tetrahydrofuran, acetone, methylene chloride. Additionally this process is not limited to solvent electrospinning as a melt-electrospinning apparatus could be used where the polymer is heated above it melting temperature ($T_m$) and electrospin in a molten state.

The electrospinning parameters can be varied significantly and can be optimized for any laboratory or commercial setting. It will therefore be appreciated that the parameters set out in table 1 are exemplary settings.

The electrospinning set-up included a programmable syringe pump Kd Scientific Model KDS 100 CE (Sandbach, Cheshire, UK), a Glassman high voltage power supply series WR (Glassman, Bramley, Hampshire, UK), a static metallic plate to collect randomly aligned fibre scaffolds. Electrospinning was carried out under standard laboratory conditions of 20±3° C. and relative humidity of 50±5%.

Anisotropic Scaffold Fabrication with Varying Fibre Diameters and Alignment

To generate anisotropic scaffolds, a combination of varying fibre alignment and fibre size were performed by either 1) sequentially electrospinning different polymer solutions onto the same mandrel at different rotation speeds or 2) laminating separate electrospun scaffolds with 2% agarose gel (Type VII, Sigma).

To fabricate sequential electrospun constructs, 10 mls of solution C was electrospun and collected on the mandrel at a speed of 1800 rpm, followed by a second volume of solution C collected at 20 rpm, and a final volume of solution D collected at 20 rpm.

To fabricate laminated electrospun constructs, individual scaffolds of solutions C, C, and D were collected at either 1800, 20, or 20 rpm, respectively. Individual scaffolds were punched using a 10 mm diameter punch, and laminated with 100 μl of molten agarose between each scaffold layer.

To assess fibre alignment of electrospun materials, small angle light scattering was employed to evaluate the orientation within fibre laminates collected at either 20 rpm or 1800 rpm. As shown in FIG. 1, electrospun fibres collected at 20 rpm displayed a random pattern of scattered light with no preferred fibre orientation while electrospun fibres collected at 1800 rpm displayed preferential alignment with a corresponding vector map.

Scaffold Characterization

Electrospun scaffolds were imaged using a JEOL 5610 environmental scanning electron microscope (SEM). Specimens were coated with 100 Å Au using an Emitech K550 sputter coater and observed under SEM at an accelerating voltage of 20 kV and a working distance of 10 cm. Fibre diameter and pore size were determined from 5 representative images using NIH Image J Software (NIH, Bethesda, Md., USA). Pore size was estimated by measuring the void space between fibre interstices.

Figure 1A:
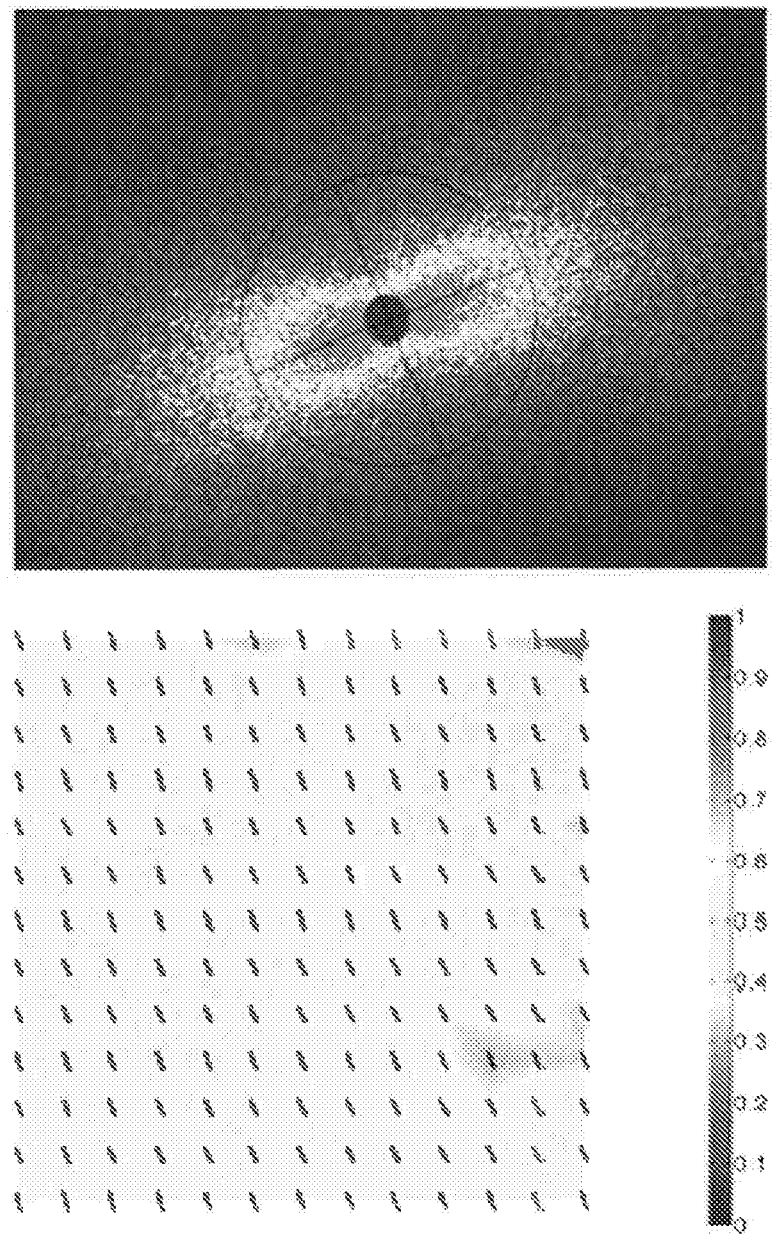
Figure 1B:
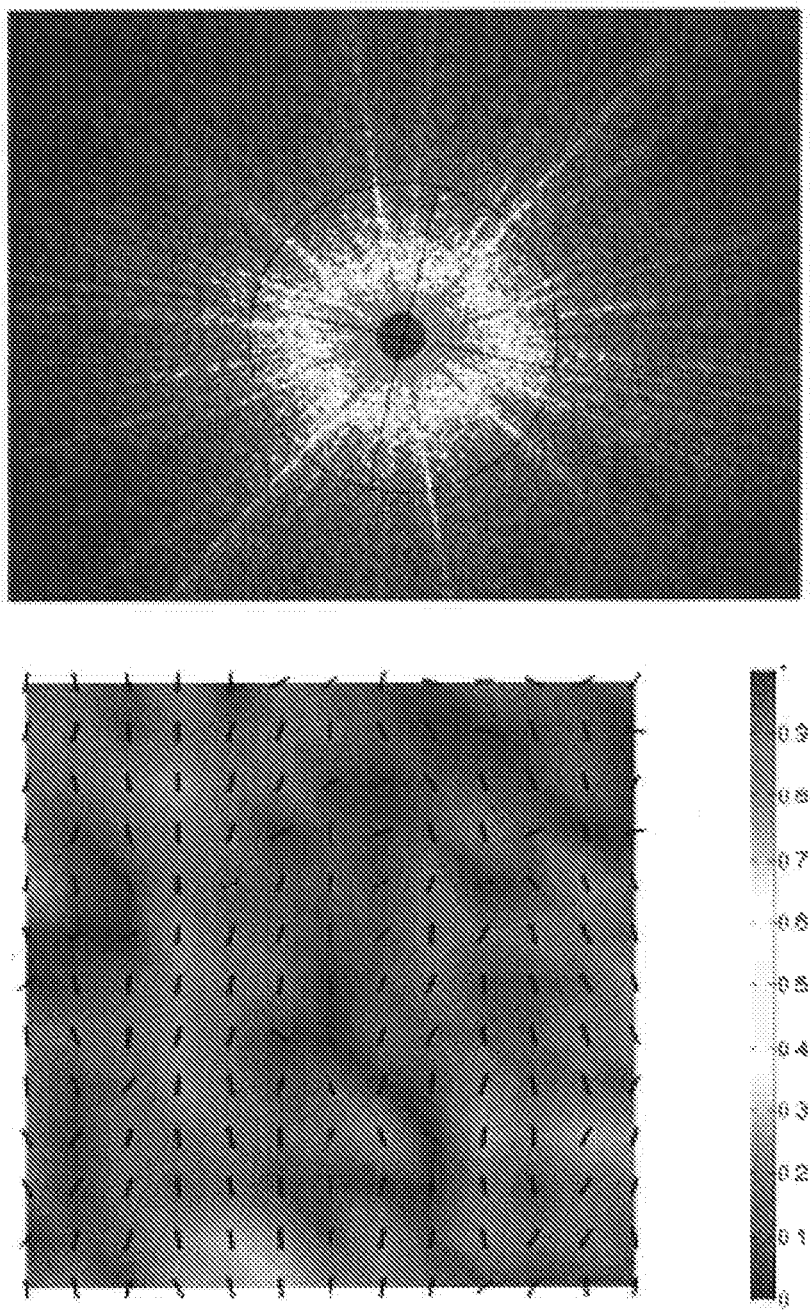
Figure 1C:
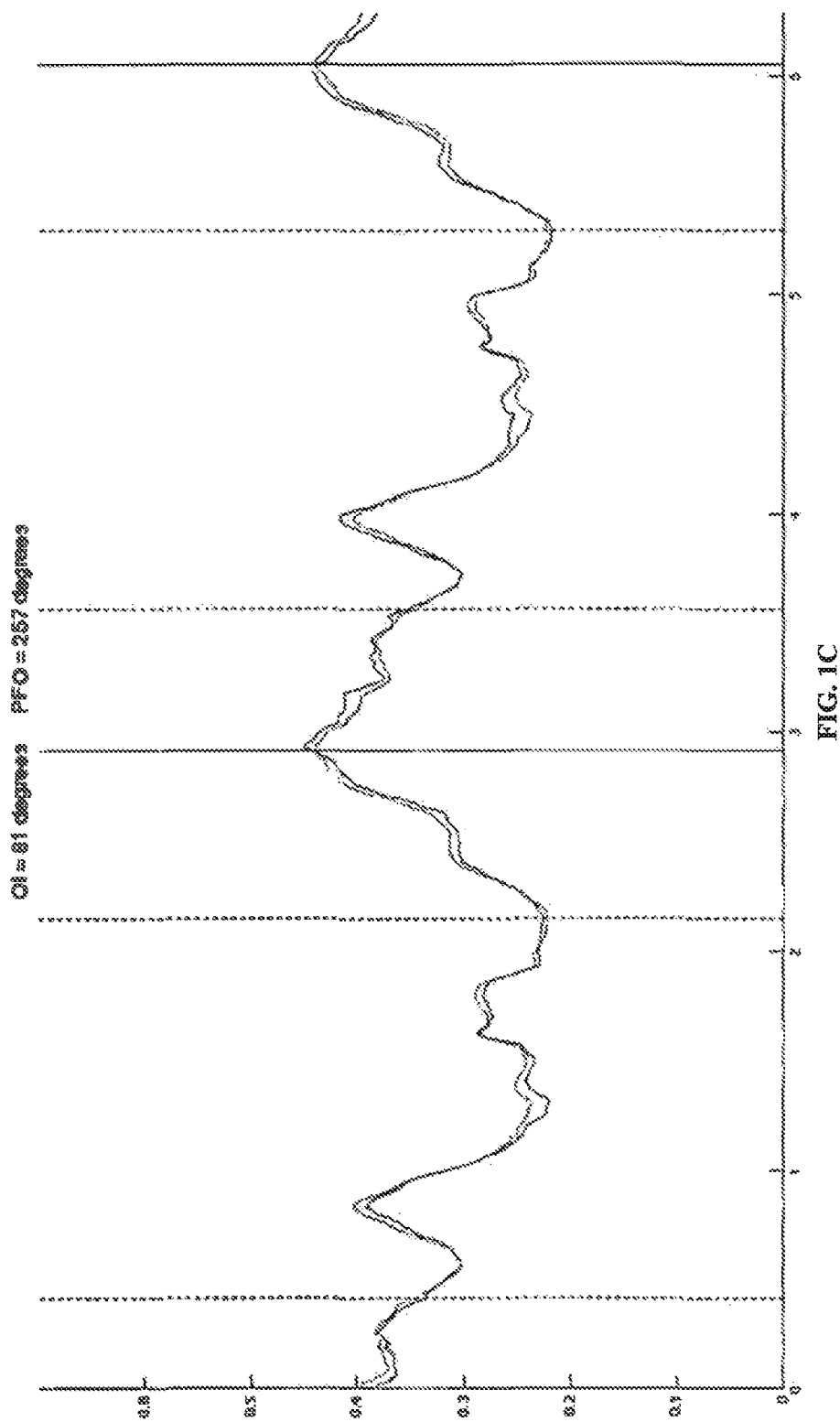
Figure 1D:
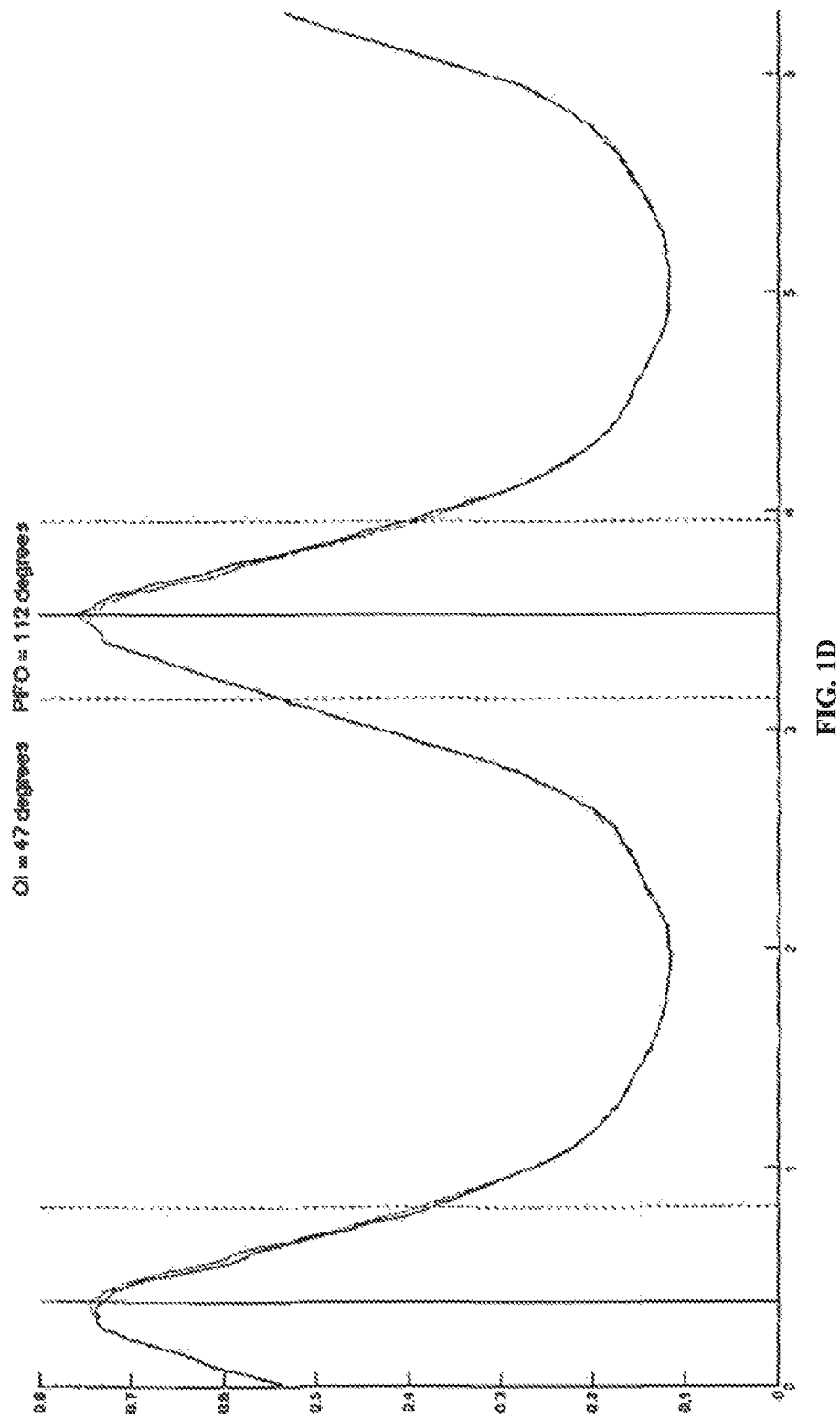
Figure 2:
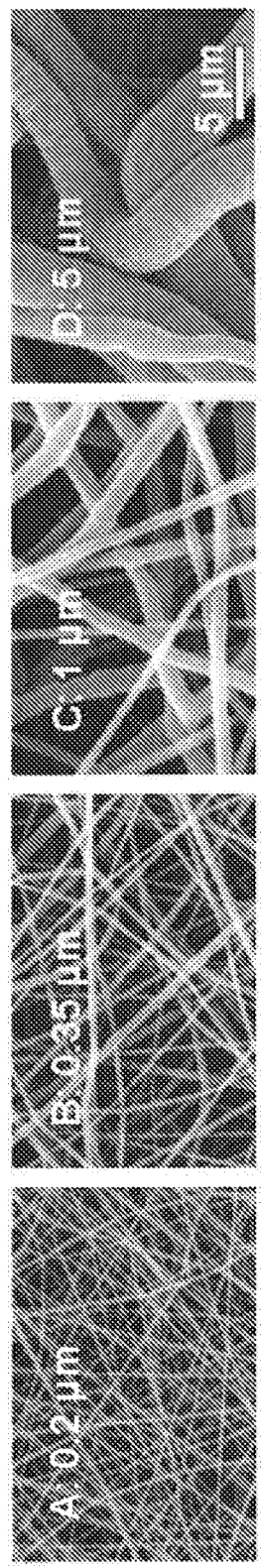
FIG. 2 shows scanning electron microscopy images of electrospun poly(caprolactone) with varying fibre sizes (A=0.2 μm, B=0.35 μm, C=1 μm and D=5 μm).
Figure 3:
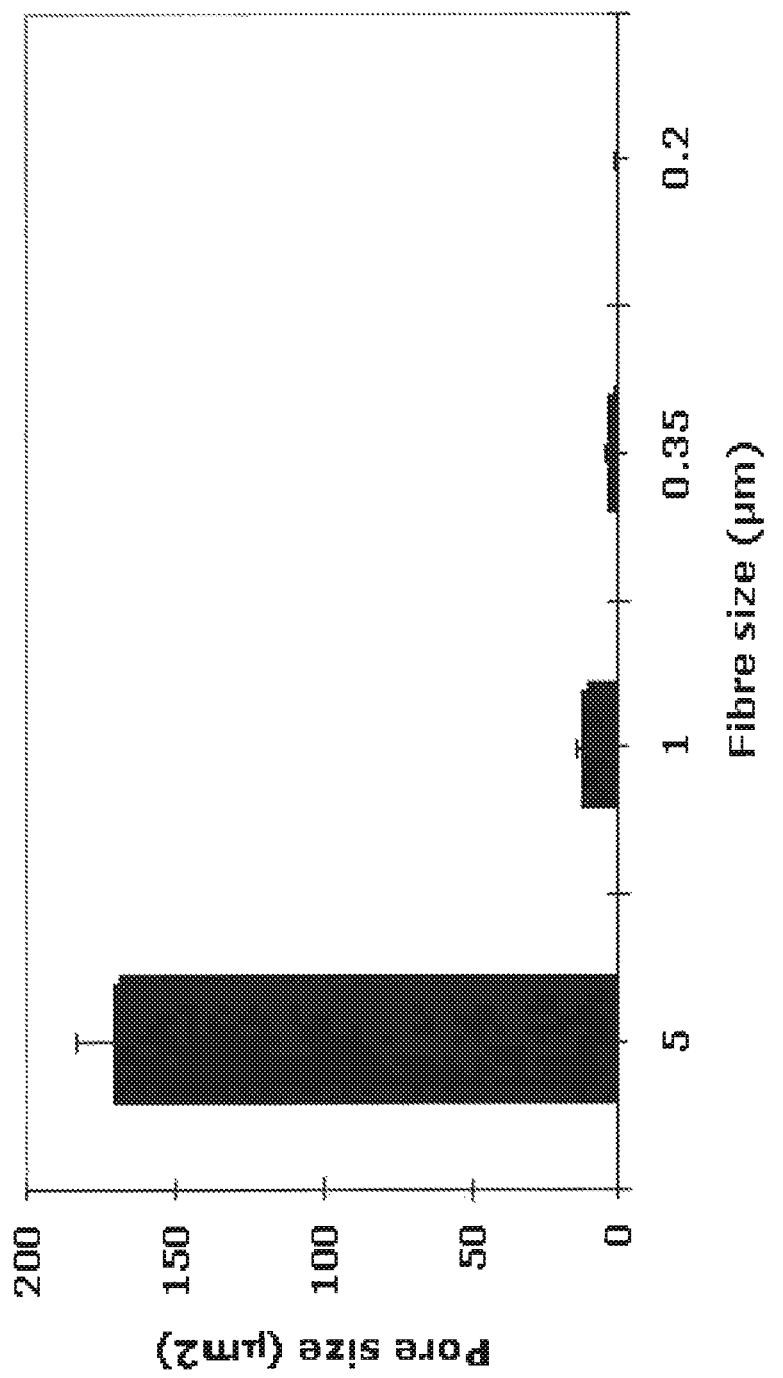
FIG. 3 shows a plot of the effect of fibre diameter on electrospun scaffold pore size.

Electrospun fibres of varying diameter were created by varying polymer solution concentration and operational parameters as outlined in Table 1. Representative electron microscopy images are shown in FIG. 2. As fibre diameter increases, the pore size of the bulk structure also increases as the fibre packing becomes less dense resulting in larger pores (FIG. 3).

Mechanical Testing

Figure 4:
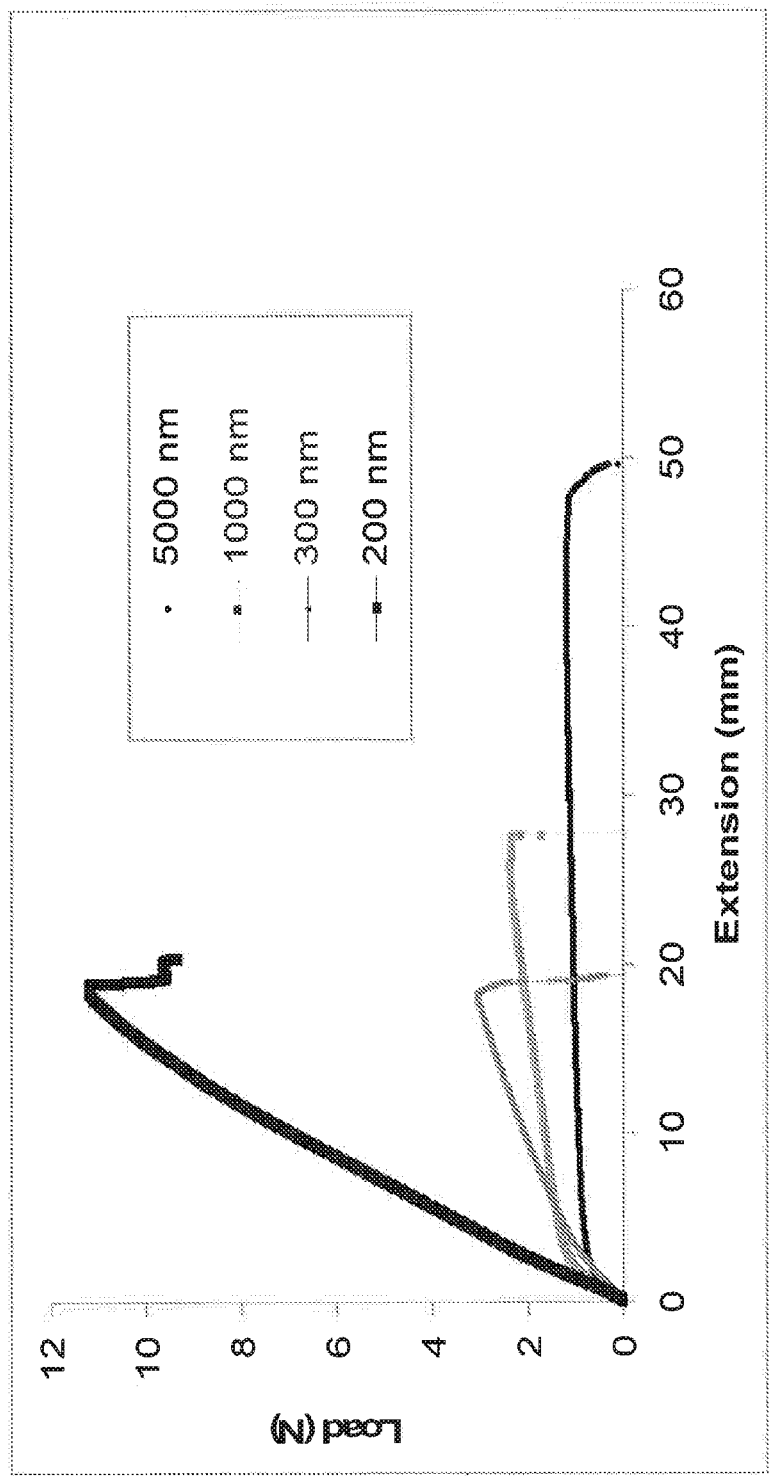
FIG. 4 shows representative load-extension curves of randomly aligned electrospun poly(caprolactone) scaffolds with varying fibre diameters.
Figure 5:
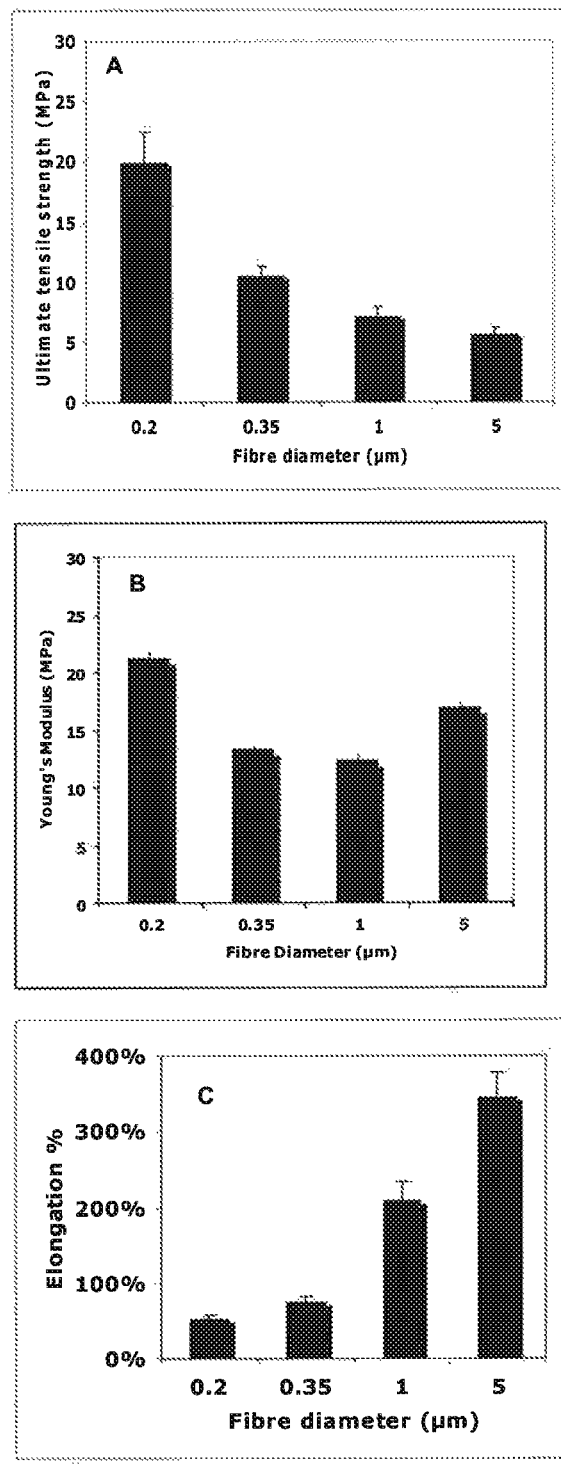
FIG. 5 shows plots of how tensile properties of electrospun poly(caprolactone) scaffolds are affected by fibre size, as tensile strength (A) and Young's modulus (B) decrease with increasing fibre size, while elongation (C) increases with fibre size accordingly.

Randomly aligned electrospun scaffolds of varying fibre diameter were mechanically tested in tension (10 mm×50 mm×0.2 mm) to failure using an Instron Model 5540 testing machine, equipped with a 50 N load cell at a crosshead speed of 10 mm/min. Specimens had a gauge length of 30 mm and thickness was measured by digital calipers and confirmed by cross-sectional SEM. The ultimate tensile strength, maximum load, Young's modulus, and elongation at break were determined from the stress-strain curves (n=10/treatment). Bulk compressive properties of layered constructs (Ø6 mm×1 mm were characterized by compressing between two impermeable platens at a rate of 0.05% strain/second up to 50% strain and compressive modulus was determined. In addition to changes in pore size, the mechanical properties of electrospun scaffolds significantly varies as a function of fibre size with smaller fibres able to withstand significantly higher loads while exhibiting much lower extension (FIG. 4, which shows representative load-extension curves of randomly aligned electrospun scaffolds with varying fibre diameters). From FIG. 4 we are able to calculate tensile strength, tensile modulus and elongation of the scaffold materials (FIG. 5). By simply varying polymer solution concentration, we can vary the size of the produced fibres which can alter the mechanics of the bulk electrospun scaffolds. FIG. 5 shows that tensile properties of electrospun scaffolds are significantly affected by fibre size as tensile strength (A) and Young's modulus (B) decrease with increasing fibre size, while elongation (C) increases with fibre size accordingly.

To assess the interfacial strength of laminated electrospun scaffolds, individual laminates of 2% agarose, aligned/aligned scaffolds, random/aligned scaffolds, or random/random scaffolds were bonded together using 100 μl molten agarose (2%). Layered laminates were tested in lap-shear mode to determine the interfacial strength and shear modulus. Stresses and strains were calculated from sample geometry, displacements, and loads. Shear strength was calculated as the maximum value of shear stress the sample endured prior to failure. Shear modulus was determined as the slope of the linear region of the stress-strain curve (n=10/treatment).

Assessment of Cell Adhesion and Morphology

To determine the effects of fibre size and chemistry on cellular adhesion and morphology, adult human chondrocytes (passage 2) were purchased from European Collection of Cell Cultures (ECACC) (Cell Line HC 402-05a) and cultured in low glucose DMEM (Dulbecco's Modified Eagle Medium), supplemented with 10% v/v fetal bovine serum, 1 mM L-proline, and 50 μg/ml ascorbic acid. Chondrocytes were seeded onto scaffolds of various fibre sizes that had been treated with or without type II collagen (10 μg/ml for 12 hrs). After 24 and 72 hrs, samples were fixed in 4% glutaraldehyde for 15 mins, rinsed 3× with phosphate buffered saline (PBS), permeabilized with 0.2% Tween-20 in 0.5% bovine serum albumin in PBS for 20 mins, stained with Oregon Green 488 phalloidin to visualize actin (1:150 in PBS; Molecular Probes, OR, USA) and counterstained with 4',6-diamidino-2-phenylindole (DAPI, Vector Laboratories, CA, USA) to visualize cell nuclei. Images were digitally captured on a Leica microscope unit equipped with filters for red, green and blue fluorescence.

Figure 6:
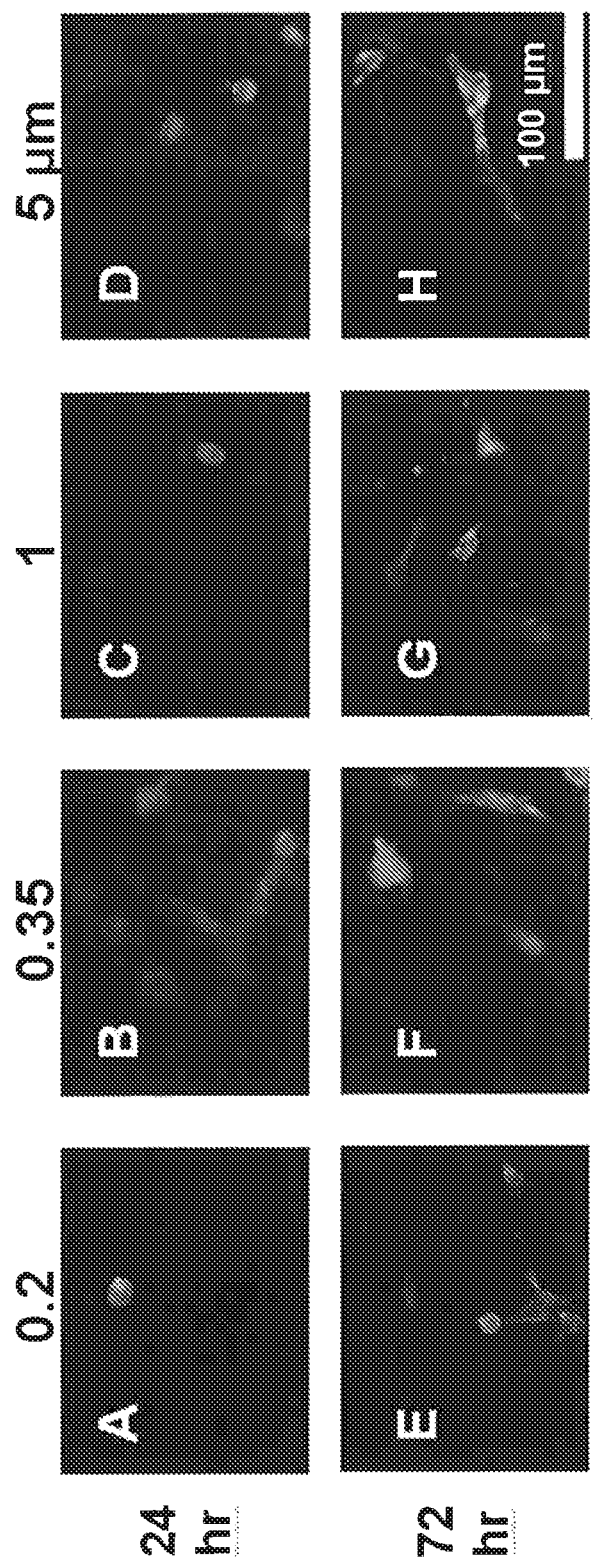
FIG. 6 shows images of human chondrocytes seeded on unmodified electrospun poly(caprolactone) (PCL) scaffolds with varying fibre diameters.
Figure 7:
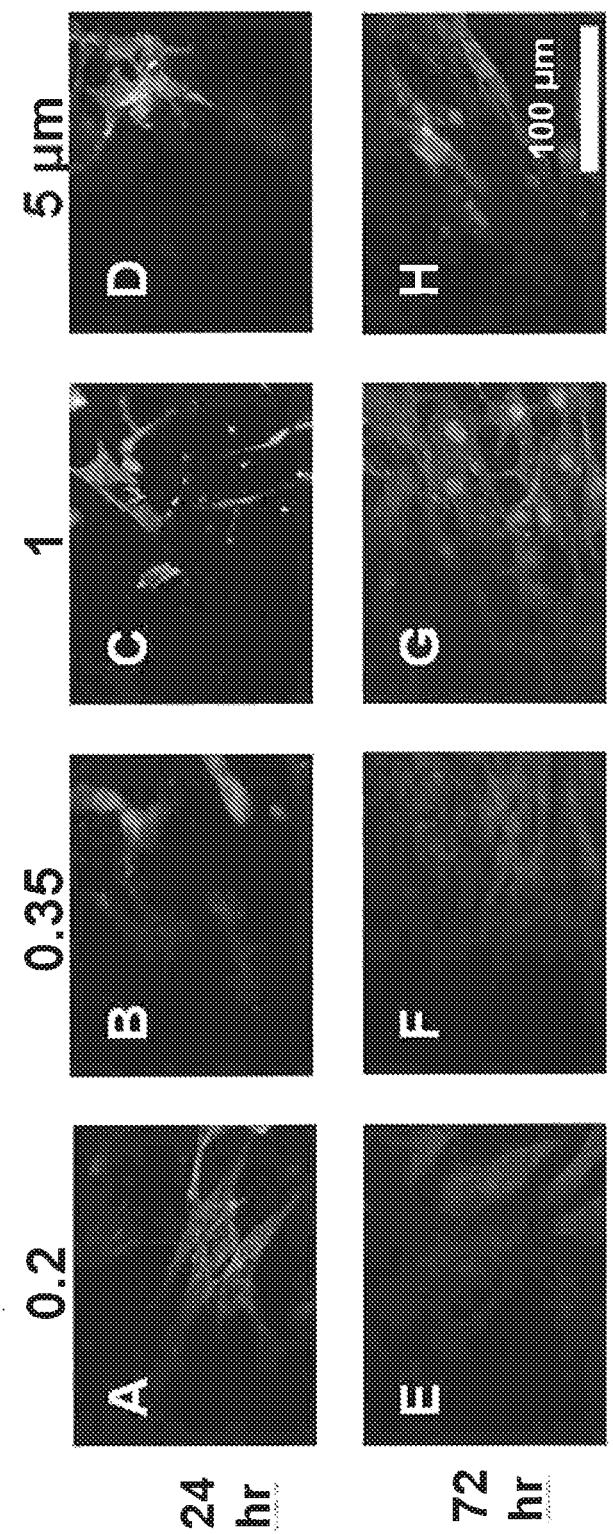
FIG. 7 shows images of human chondrocytes seeded on modified electrospun poly(caprolactone) scaffolds with varying fibre diameters, treated with type II collagen. Chondrocyte adhesion was improved for all conditions compared to unmodified poly(caprolactone) scaffolds.

In line with the procedure described above, human chondrocytes were seeded onto electrospun PCL scaffolds of varying fibre size that had been treated with or without type II collagen. Without the addition of type II collagen minimal cells were able to adhere to the scaffolds and cells exhibited a rounded morphology after 24 and 72 hrs in vitro (FIG. 6). Electrospun scaffolds treated with type II collagen had a much higher number of cells compared to untreated scaffolds and were able to form near confluent layers within and on the scaffolds. No difference was observed between fibre diameters (FIG. 7).

Assessment of In Vitro Chondrogenesis

To determine the effect of fibre size on human chondrocytes (passage 4), human chondrocytes were seeded at 100,000 cells/cm$^2$ on scaffolds and cultured in chondrogenic differentiation medium which consisted of DMEM (4.5 g/L 1-glucose) supplemented with 40 µg/ml L-proline, 50 µg/ml ascorbic acid, 0.1 mM sodium pyruvate, 10 ng/ml TGF-β3, and 1% v/v ITS Premix (BD Biosciences). Medium was changed twice weekly. After 7, 21, 35 days of culture, cell-seeded scaffolds were digested in a papain digest (2.5 units papain/ml, 5 mM cysteine HCl, 5 mM ethylenediaminetetraacetic acid (EDTA), in PBS) at 60° C. overnight. Digested samples were assayed for total DNA content using the Quant-iT™ PicoGreen® kit (Invitrogen, Paisley, UK). Sulfated glycosaminoglycans were determined using the Blyscan Kit (Biocolor, Carrickfergus, UK) per manufacturer's instructions.

Figure 8:
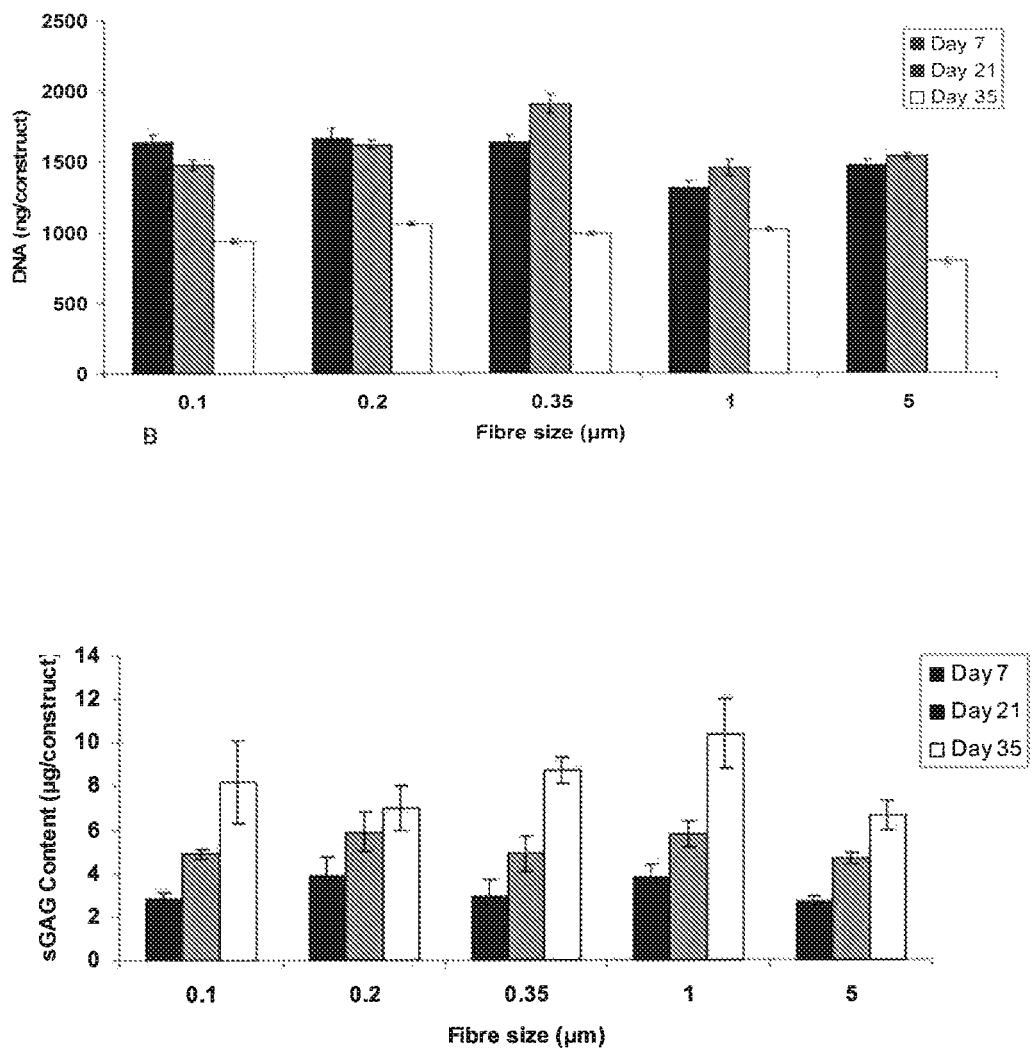
FIG. 8 shows the biochemical content of cell-seeded scaffolds after 7, 21, and 35 days culture for DNA (ng/construct) and sulfated glycosaminoglycans (μg/construct).

Using the procedure described above, human chondrocytes were cultured in vitro on electrospun PCL scaffolds to assess if fibre diameter affected chondrogenesis as measured by sulfated glycosaminoglycan (GAG) content. On days 7, 21, and 35, DNA content (A) and sulfated GAG content (B) were quantified (FIG. 8). DNA content remained constant over the first three weeks of culture but dropped significantly by day 35, likely due to apoptosis. Sulfated GAGs increased in a temporal fashion but did not exhibit any significant differences between fibre sizes indicating that fibre size did not play a significant role in promoting in vitro chondrogenesis.

critical step is that the fibres laminates must be comprised of at least three layers with differing fibre size, fibre alignment, and mechanical properties in terms of Young's modulus, ultimate tensile strength, and elongation. As shown in FIG. 9, sequential electrospinning of solutions C, C, and D yields a structure resemblant of the collagen framework within articular cartilage. Bulk compressive testing also indicates that this design is within the compressive modulus range for articular cartilage (Table 3).

As outlined in Tables 2 and 3, electrospun scaffolds can emulate the zonal mechanical properties of articular cartilage and create a natural anisotropic gradient that preserves a gradient with fibre orientation, tensile strength, and tensile modulus.

TABLE 2

Representative mechanical properties of human articular cartilage

| Cartilage Zone | Fibre Orientation | Tensile Stress (MPa) | Tensile Modulus (MPa) | Compressive Modulus (MPa) | Shear Modulus (MPa) |
| --- | --- | --- | --- | --- | --- |
| Superficial | Parallel | 35.5 | 10.2 | 0.1-2 | 0.68 |
| Middle | Random | 15 | 3.2 | | |
| Deep | Perpendicular | 10 | 0.87 | | |

TABLE 3

Mechanical properties of electrospun equivalent zones for the anisotropic, zonal cartilage scaffold.

| Cartilage Zone | Electrospun Equivalent | Fibre Orientation | Tensile Stress (MPa) | Tensile Modulus (MPa) | Compressive Modulus (MPa) | Shear Modulus (MPa) |
| --- | --- | --- | --- | --- | --- | --- |
| Superficial | Ø1 µm | Aligned | 35 ± 2 | 85 ± 3.8 | 0.15 ± 0.5 | 0.25 ± 0.5 |
| Middle | Ø1 µm | Random | 7.4 ± 0.7 | 12.4 ± 4.4 | | |
| Deep | Ø5 µm | Random | 5.7 ± 0.4 | 17 ± 3.9 | | |

Statistics

All experimental sample groups had a sample size of at least n=3 and experiments were performed in two independent trials using human chondrocytes. Data is presented as average±standard error mean. Statistical significance was determined by performing ANOVA and Tukey HSD tests with a significance accepted at a p-value <0.05.

Creating Layered Constructs with Zonal Tensile Properties by Sequential Electrospinning To create anisotropic scaffolds that can mimic zonal tensile properties of type II collagen and feature varying fibre alignment, sequential electrospinning of different polymer solutions or under different operational parameters can be performed to generate dense fibre networks. These networks create zone specific, depth-dependent regions with varying tensile properties, fibre/pore size, and can feature varying fibre alignment to mimic the anisotropic properties and morphology of articular cartilage. By mimicking the zonal tensile properties of articular cartilage we are able to provide a mechanically functional equivalent. By varying collector speed we are able to create fibrous laminates that are either aligned or randomly oriented based on the plurality of fibres being oriented in single direction or completely non-oriented.

By combining fibre laminates of different orientations and different sizes we are able to generate depth-dependent properties for electrospun scaffolds. Thus, for this application the Creating Layered Constructs with Zonal Tensile Properties by Individual Layer Fabrication and Lamination In addition to performing sequential electrospinning, individual bulk fibre scaffolds can be fabricated and laminated using a biocompatible hydrogel as shown in FIG. 10.

Techniques such as laser ablation or micromachining of pores can be employed to assist with gel permeation between the layers and thereby reduce any tendency of individual scaffold layers to separate due to shearing between the different layers.

To assess the shear strength and Young's modulus of the laminated scaffolds, agarose gel was cast between the electrospun scaffolds and lap shear testing was performed on various combinations of fibre laminates as illustrated in FIG. 11.

The addition of the electrospun laminates significantly increased the interfacial strength (FIG. 12A) when compared to the agarose laminates, but did not affect the Young's modulus (FIG. 12B) as the stiffness of the laminates was purely attributed to the gel phase in between the electrospun scaffolds.

Assessment of In Vitro Chondrogenesis for Sequentially Generated Layered Construct A long term chondrogenic experiment was carried out with freshly isolated bovine chondrocytes. After 21 days in vitro, chondrocytes are able to remain largely viable and penetrate into the sequentially formed layered construct (FIG. 13). The experimental protocol used in this assessment was the same as described above for electrospun PCL scaffolds.

Exemplification Data for PLA

In addition to fabricating the construct from PCL, other polymer systems can be used such as poly(1-lactic acid) (PLA). PLA with an inherent viscosity ~2.0 dl/g (Sigma) was dissolved in HFIP and electrospun at varying conditions to generate electrospun PLA fibres of varying sizes (Table 4).

TABLE 4

Electrospinning parameters for generating varying fibre diameters from PLA.

| Solution | Target fibre diameter (μm) | Solvent | PLA (wt/v %) | Flow rate (mL/hr) | Voltage (kV) | Collection Distance (cm) | Needle |
|---|---|---|---|---|---|---|---|
| A | 1 | HFIP | 8 | 3 | 15 | 10 | 19 |
| B | 2 | HFIP | 12 | 3 | 15 | 10 | 16 |
| C | 5 | HFIP | 16 | 3 | 19 | 10 | 16 |

Electrospun scaffolds were imaged using a JEOL 5610 environmental scanning electron microscope (SEM). Specimens were coated with 100 Å Au using an Emitech K550 sputter coater and observed under SEM at an accelerating voltage of 20 kV and a working distance of 10 cm. Fibre diameter were determined from 5 representative images using NIH Image J Software (NIH, Bethesda, Md., USA).

Mechanical Testing of Electrospun PLA

Randomly aligned electrospun scaffolds of PLA at varying fibre diameter were mechanically tested in tension (10 mm×50 mm×0.2 mm) to failure using an Instron Model 5540 testing machine, equipped with a 50 N load cell at a crosshead speed of 10 mm/min. Specimens had a gauge length of 30 mm and thickness was measured by digital calipers and confirmed by cross-sectional SEM. The ultimate tensile strength, maximum load, Young's modulus, and elongation at break were determined from the stress-strain curves (n=10/treatment).

Fibre size plays an important parameter in the bulk tensile properties of electrospun scaffolds. For electrospun PLA materials, tensile modulus decreases with increasing fibre size (B), while elongation increases with fibre size (C). No major differences were determined for ultimate tensile strength for electrospun PLA relative to fibre size. Moreover when polymer concentration is plotted versus fibre diameter for both PLA and PCL, a direct correlation can be seen between these two different polymer systems. This correlation indicates that by varying polymer concentration for a variety of polymers we are able to vary fibre size, and accordingly bulk mechanical properties of the resulting constructs.

EXAMPLE 2

Scaffold Fabrication and Characterisation

Additional scaffold fabrication was carried out using PCL with a number average $M_n$, molecular weight of 80,000 Da and the solvent HFIP. PCL was dissolved in HFIP at 15 or 25 wt % overnight and then electrospun through a 16 gauge blunt tip needle collected onto a voltage-driven rotating mandrel (width=6 cm; diameter=20 cm) at a linear velocity of 0-1 or 20 m/s. To fabricate tri-laminar scaffolds, 10 ml of a 15 wt % PCL solution was electrospun and collected at a linear velocity of 20 m/s, followed by a second 10 ml volume of 15 wt % PCL collected at 0-1 m/s, and a final 10 ml volume of 25 wt % PCL collected at 0-1 m/s.

Varying the linear velocity from 20 m/s to 1 m/s did not significantly alter fibre size. The resulting fibres were either aligned or randomly oriented as determined by SEM (imaged using a JEOL 5610 environmental scanning electron microscope, as described in Example 1). Fibre and pore size were determined from 10 representative images using NIH Image J. Software. Cross-sectional examination of scaffolds by SEM was performed after freeze fracturing scaffolds immersed in liquid nitrogen.

TABLE 5

Electrospinning parameters and fibre properties for individual electrospun layers. All PCL solutions were electrospun at an applied voltage of 15 kV at a volumetric flow rate of 3 ml/hr.

| Electrospun Cartilage Equivalent | Polymer Concentration (w/v) | Working Distance (cm) | Linear Velocity (m/s) | Fiber Orientation | Fiber Size (μm) | Pore Size (μm²) |
|---|---|---|---|---|---|---|
| Superficial | 15 | 10 | 20 | Aligned | 1.1 ± 0.3 | 4.2 ± 1 |
| Middle | 15 | 10 | 0-1 | Random | 0.9 ± 0.2 | 12.9 ± 1.3 |
| Deep | 25 | 15 | 0-1 | Random | 4.5 ± 1.2 | 171 ± 102 |

Results of tensile testing are shown in Table 6. Testing was carried out using an Instron Model 5540 testing machine as described in Example 1. Specimens had a gauge length of 30 mm and width of 10 mm. Ultimate tensile strength and Young's modulus were determined from stress-strain curves where the ultimate tensile strength was taken as the maximum stress and the Young's modulus was calculated from the linear region of the stress-strain curve. Advantageously, tri-laminar composite scaffolds displayed significantly higher ultimate tensile strengths than homogeneous randomly oriented fibre scaffolds of either 1 or 5 μm in diameter, yet their tensile moduli were not significantly different.

TABLE 6

Compiled mechanical properties of bulk fibre layers.

| Electrospun Cartilage Equivalent | Fiber Size (μm) | Fiber Orientation | Tensile Stress (MPa) | Tensile Modulus (MPa) |
|---|---|---|---|---|
| Superficial | 1 | Aligned | 35.0 ± 2 | 85 ± 3.8 |
| Middle | 1 | Random | 7.4 ± 0.7 | 12.4 ± 4.4 |
| Deep | 5 | Random | 5.7 ± 0.4 | 7.0 ± 3.9 |
| Tri-laminar Composite | 1-5 | Multi | 7.8 ± 0.5 | 25.0 ± 3 |

A variation was noted between the tensile modulus for the deep scaffold above and the deep scaffold of Example 1. Subsequent scaffold fabrications and characterisations tended to give a value in the region of 7 MPa.

Bovine Chondrocyte Isolation

Bovine cartilage was harvested from the lower leg joint of young calves. Chondrocytes were isolated by digesting in DMEM+Glutamax (4.5 g/l glucose) with 0.2% w/v pronase, 10 mM HEPES, 50 µg/ml gentamycin, and 5% v/v foetal bovine serum (FBS) for 1 hr at 37° C. with agitation. This digest was removed and replaced with DMEM+Glutamax (4.5 g/l glucose) supplemented with 10 mM HEPES, 50 µg/ml gentamycin, 5% v/v FBS, and 0.04% w/v collagenase type I (Sigma) overnight at 37° C. with agitation. After digestion, isolated chondrocytes were filtered through a 70 µm pore size filter, centrifuged at 250 g for 3 mins, and plated in DMEM (4.5 g/l glucose) with 10% v/v FBS, 50 µg/ml ascorbic acid (Sigma), and 50 µg/ml gentamycin (expansion medium).

Assessment of In Vitro Chondrogenesis

Bulk electrospun sheets of tri-laminar scaffolds were fabricated (approx 1 mm thickness). 10 mm diameter scaffolds were punched from electrospun sheets, sterilised in 70% ethanol for 30 mins followed by three washes with sterile PBS and then soaked in 0.01% v/v bovine serum albumin (BSA) in PBS overnight to assist with chondrocyte adhesion. 20 µl of expansion medium containing 0.25M bovine chondrocytes (passage 1) was placed on one side of each scaffold and cells were allowed to adhere for 2 hrs before seeding the other side with an additional 0.25M chondrocytes. Following chondrocyte adhesion, scaffolds were transferred to non-adherent 24 well plates and cultured in 1 ml of chondrogenic differentiation medium consisting of DMEM (4.5 g/L 1-glucose), supplemented with 50 µg/ml L-proline, 50 µg/ml ascorbic acid, 0.1 mM sodium pyruvate, 10 ng/ml TGF-β3, and 1% v/v ITS Premix (BD Biosciences, Oxford, UK) at 37° C. and 5% $CO_2$. Medium was changed twice weekly.

Chondrocyte Viability, Morphology, and Biochemical Assessment

To evaluate the ability of bovine chondrocytes to adhere, proliferate and differentiate on tri-laminar scaffolds, Chondrocyte viability on electrospun scaffolds was assessed using the LIVE/DEAD® Cell Viability assay (Invitrogen) after 0, 1, 3, and 5 weeks in culture. Scaffolds were rinsed twice with PBS, incubated with 4 µM Calcein AM and 4 µM ethidium homodimer-1 in PBS, which stain live and dead cells green and red, respectively, and then imaged using an epifluorescence microscope. This assay demonstrated high cell viability throughout the 5 weeks.

Chondrocyte morphology on electrospun scaffolds was assessed by examining cytoskeletal organisation by immunostaining. Scaffolds were fixed in 4% w/v paraformaldehyde for 15 mins, washed twice with PBS, and permeabilised with 0.25% v/v Triton X-100 in PBS for 15 mins. Actin cytoskeleton was stained with Alexa Fluor® 568 phalloidin (Invitrogen; 1:160) for 20 mins and nuclei were stained with DAPI (Sigma; 1:1000) for 2 mins. Type I and type II collagen were detected using Collagen I antibody (rabbit polyclonal, Ab34710) and Collagen II antibody (dilution ratio 1:100, rabbit polyclonal, Ab34712, Abcam, Cambridge, UK). Both antibodies were detected using Goat polyclonal secondary antibody to rabbit IgG with a FITC conjugation (Ab97050) (dilution ratio 1:1000) and counterstained with DAPI (Sigma; 1:1000) for 2 mins. Sections were stained separately for collagens and imaged on an epifluorescence microscope. Chondrocytes assumed an aligned morphology on the aligned fibre side of tri-laminar scaffolds, but did not exhibit this alignment on the randomly oriented zone and instead exhibited spread morphologies.

To quantify the number of chondrocytes on scaffolds, DNA content was measured post-seeding and after 1, 3, and 5 weeks in culture. After 0, 1, 3, and 5 weeks, chondrocyte-seeded scaffolds were digested in papain digest (2.5 units papain/ml, 5 mM cysteine HCl, 5 mM EDTA, in PBS (All reagents from Sigma)) at 60° C. overnight. Digested samples were assayed for total DNA content using the Quant-iT™ PicoGreen® kit (Invitrogen). Sulfated glycosaminoglycan (GAG) contents were determined using the Blyscan Kit (Biocolor, Carrickfergus, UK). Chondrocyte adhesion was not significantly different among samples following seeding, and chondrocyte number increased significantly after 1 and 3 weeks. DNA content increased significantly following 1 and 3 weeks but no further increases were noted at week 5 (FIG. 17A). By week 5 all scaffolds demonstrated decreases in chondrocyte DNA content compared to week 1. However the DNA content on all scaffolds was still greater after 5 weeks than that measured immediately post seeding. Total GAG content increased between post-seeding and week 1 for all groups. At weeks 3 and 5, total GAG content was significantly higher comparative to post-seeding levels and week 1 for all groups (FIG. 17B). GAG content normalised to DNA content displayed significant enhancements at week 3 and 5 comparative to week 1 (FIG. 17 C), indicating significant chondrocyte differentiation.

Histological Examination of Chondrocyte-Seeded Scaffolds

After 5 weeks in culture, tri-laminar composite scaffolds were embedded in Tissue-Tek® OCT (Fischer Scientific, Loughborough, UK) freezing medium and flash frozen in isopentane. Scaffolds were sectioned at 10 µm and stained for deposited sulfated proteoglycans (GAGs) using 0.1 wt % Alcian Blue (pH 1) or for collagen with Picrosirius Red. Histological examination revealed variations in both collagen and GAG distribution, with preferential deposition in the superficial (aligned 1 µm) and deep zones (random 5 µm). Production and secretion of type II collagen was present on all scaffold types as revealed by immunohistochemical staining, with minimal staining for type I collagen.

Gene Expression Analysis

After weeks 0, 1, 3 and 5, total RNA was isolated from the scaffolds using a RNeasy kit and cDNA was obtained from reverse transcription using the QuantiTect Reverse Transcription kit (all from Qiagen, UK). Real-time quantitative PCR was carried out on a Rotorgene Corbett PCR, using previously published primer sequences. qPCR were performed on Glyceraldehyde-3-phosphate dehydrogenase (GAPDH) (U85042, forward: ACCCTCAAGATTGTCAGCAA, reverse: ACGA TGCCAAAGTGGTCA), Aggrecan (AGC, U76615, forward: GCTACCCTGACCCTTCATC, reverse: AAGCTTTCTGGGA TGTCCAC), Col1α1 (NM-174520, forward: CATTAGGGGTCACAATGGTC, reverse: TGGAGTTCCA TTTTCACCAG) and Col2α1 (X02420, forward: CATCCCACCCTCTCACAGTT, reverse: GTCTCT-GCCTTGACCCAAAG) using the QuantiTect SYBR Green PCR kit. Primers were validated and the efficiencies of the primers have been found between 0.90 and 1.07. The gene expression levels were normalised to the expression of the housekeeping gene GAPDH and were expressed as fold changes relative to week 0 control samples. The relative mRNA levels of Aggrecan, Col2α1 and Col1α1 were calculated using the ΔΔCt method and the Col2α1/Col1α1 ratio corresponds to the $2^{-\Delta Ct}$ each gene.

mRNA levels of aggrecan and Col2α1 were significantly increased from week 1 and up to week 5. Expression of Col1α1 decreased after week 1 and continued to decrease up to week 5. Furthermore, expression of Col2α1 increased up to week 3. As a result, the ratio of expression Col2α1/Col1α1, increased significantly during the experiment time course. All scaffolds sustained chondrogenic gene expression, an indicator of maintenance of chondrocyte phenotype.

Statistical Analysis

All experimental groups had a sample size of at least n=4 for biochemical, qPCR and histological analyses and n≥5 for mechanical property analyses. Data are presented as average±standard error mean. Statistical significance was determined by performing ANOVA and Tukey HSD tests with a significance accepted at a p-value<0.05.

Discussion

Tri-laminar composite scaffolds yielded significantly higher ultimate tensile strengths than randomly oriented small (1 µm) or large (5 µm) fibre diameter homogenous scaffolds, which suggests that the addition of the aligned superficial region significantly contributed to the tensile properties of the bulk scaffold.

All scaffolds supported chondrocyte attachment and viability after up to 5 weeks in culture, demonstrating that the material system and fabricated scaffolds were biocompatible. Nevertheless, cell morphology varied depending on fibre organisation, with tri-laminar scaffolds fostering aligned cell morphologies in the superficial zone and spread in the randomly oriented deep zone of the scaffold. While chondrocytes in native cartilage tend to have rounded morphologies, the addition of adsorbed proteins (such as BSA) to scaffolds to promote cell attachment in the present study likely promoted the more spread morphologies observed here. The use of fibrous scaffolds combined with hydrogels may preclude the need for protein adsorption on scaffolds and may be a more effective means to maintain cells with native tissue-like morphologies within fibrous scaffolds.

In addition to promoting cell attachment and viability, all scaffolds examined also supported chondrocyte proliferation and GAG production. Production and secretion of type II collagen was present on all scaffolds with minimal staining for type I collagen. These results indicated maintenance of chondrocyte phenotype on the scaffolds. Tri-laminar scaffolds supported chondrocyte proliferation and the production of a GAG-rich extracellular matrix that upon quantification was not significantly different from that produced in homogenous scaffolds. This demonstrates that variations in fibre orientation and size in a continuous scaffold do not impede cell attachment and proliferation or GAG production, while still providing the mechanical and morphological cues of a more native tissue-like organisation. The data produced suggests that depth-dependent variation in fibre size and orientation influence extracellular matrix deposition and organisation, producing engineered scaffolds with more similarities to native cartilage than that observed in homogenous scaffolds.

In conclusion, the results suggest that the fibrous scaffolds of the invention could be useful in developing regenerative medicine strategies to treat articular cartilage lesions.

It will be appreciated to a skilled person reading this disclosure that various changes in form and detail can be made without departing from the true spirit and scope of the invention and such changes are encompassed by the invention.

The invention claimed is:

1. A layered construct for repairing or replacing cartilage or cartilage-like tissue, the construct comprising a first layer, a second layer and a third layer, wherein the second layer is located between the first layer and the third layer, wherein:
   the first layer comprises aligned polymeric fibers that provide anisotropic tensile properties, such that tensile strength of the first layer is greater in a direction substantially perpendicular to the direction of layering than in the direction of layering;
   the second layer and the third layer comprise randomly oriented polymeric fibers; and
   the average diameter of fibers within the third layer is greater than the average diameter of fibers within the second layer by a factor of 2 or more.

2. The layered construct according to claim 1, wherein the polymeric fibers of the first layer are aligned substantially perpendicular to the direction of layering.

3. The layered construct according to claim 1, wherein the average diameter of fibers within the first, second and third layers are: first layer 0.1-5 µm; second layer: 0.1-5 µm; and third layer: 0.5-25 µm.

4. The layered construct according to claim 1, wherein the second and third layers each independently has a tensile modulus and/or tensile strength that is lower by a factor of 2 or more compared to the tensile modulus and/or tensile strength, respectively, of the first layer.

5. The layered construct according to claim 1, wherein the tensile modulus of the third layer is equivalent to, greater than or lower than the tensile modulus of the second layer.

6. The layered construct of claim 5, wherein the tensile modulus of the third layer is lower than the tensile modulus of the second layer.

7. The layered construct according to claim 1, wherein the tensile modulus of each layer is: first layer: 10-100 MPa; second layer: 3-20 MPa; and third layer: 0.5-20 MPa.

8. The layered construct according to claim 1, wherein the tensile strength of the third layer is equivalent to or lower than the tensile strength of the second layer.

9. The layered construct of claim 8, wherein the tensile strength of the third layer is lower than the tensile strength of the second layer.

10. The layered construct according to claim 1, wherein the tensile strength of each of the layers is: first layer: 10-200 MPa; second layer: 5-60 MPa; and
    third layer: 3-20 MPa.

11. The layered construct according to claim 1, wherein the tensile strength of the construct is 5-30MPa and the tensile modulus of the construct is 5-50MPa.

12. The layered construct according to claim 1, wherein the polymeric fibers of the first layer, second layer and third layer are each formed from a biocompatible and biodegradable polymer, optionally selected from the group consisting of poly(caprolactone), poly(lactic acid), poly(glycolic acid), poly(2-hydroxyethyl methacrylate), polydioxanone, poly(3-hydroxybutyrate), poly(3-hydroxyvalerate), poly(valcrolactone), poly(tartronic acid), poly(β-malonic acid), poly(propylene fumarate), polyanhydrides, tyrosine-derived polycarbonates, polyorthoesters, olyphosphazenes, poly (glutamic acid), collagen, hyaluronic acid, fibrin, alginate, laminin, elastin, chitosan, silk, keratin, cellulose, collagen and a copolymer or mixture of any of the polymers mentioned above.

13. The layered construct according to claim 12, wherein the polymer used to form the polymeric fibers is provided at a molecular weight ($M_w$) from 10,000 to 600,000 Daltons.

14. The layered construct of claim 12, wherein the polymeric fibers of the first layer, second layer and third layer are each formed from poly(caprolactone).

15. The layered construct according to claim 1, wherein the construct comprises one or more additional layers.

16. The layered construct according to claim 15, wherein the construct comprises a base layer adjacent the third (deep) layer, wherein the base layer comprises an inorganic material.

17. The layered construct of claim 16, wherein the base layer comprises an inorganic material selected from the group consisting of calcium phosphate and a bioactive glass.

18. The layered construct according to claim 1, wherein the construct further comprises an additional component integrated within one or more of the first, second and third layers, wherein the additional component can be selected from the group comprising decellularized xenogenic or allogenic tissue components, a growth factor, a protein or peptide, a hydrogel, a carbohydrate, an inorganic bioactive compound such as a bioactive glass or calcium phosphate crystals.

19. The layered construct according to claim 1, wherein the construct is seeded with cells.

20. The layered construct according to claim 1, wherein the thickness of the construct is from 0.5-3 mm and wherein the specific thicknesses of each layer, in terms of proportion of the overall thickness of the construct, are approximately the following:
    first layer: 10-30%;
    second layer: 20-40%;
    third layer: 30-70%.

21. A device comprising the layered construct of claim 1 wherein the device is a cartilage scaffold or an osteochondral plug.

22. The layered construct of claim 1, wherein the cartilage or cartilage-like tissue is articular cartilage.

23. A process of producing a layered construct, the process comprising:
    a) electrospinning a polymer to form a first layer of polymer fibers,
    b) electrospinning a polymer to form a second layer of polymer fibers, and c) electrospinning a polymer to form a third layer of polymer fibers, wherein: the construct is assembled to have the second layer positioned between the first layer and the third layer; the first layer comprises aligned polymeric fibers that provide anisotropic tensile properties, such that tensile strength of the first layer is greater in a direction substantially perpendicular to the direction of layering than in the direction of layering; the second layer and the third layer comprise randomly oriented polymeric fibers; and the average diameter of fibers within the third layer is greater than the average diameter of fibers within the second layer by a factor of 2 or more.

24. The process according to claim 23, wherein the electrospinning parameters are chosen such that the layers have one or more of the following properties:
  i) the average diameter of fibers within the third layer is greater than the average diameter of fibers within the second layer;
  ii) the second layer and the third layer have a tensile modulus and/or tensile strength that is significantly lower, by a factor of 2 or more, compared to the first layer.

25. The process according to claim 23, wherein the process is a solvent electrospinning process in which a first polymer solution, second polymer solution and third polymer solution are electrospun to produce the first, second and third layers, respectively, or wherein the process is a melt-electrospinning process, where the polymer is heated above its melting temperature ($T_m$) and electrospun in a molten state.

26. The process according to claim 25, wherein the first, second and/or third polymer solutions comprise an additional component selected from the group comprising decellularized xenogenic or allogenic tissue components, a growth factor, a protein or peptide, a hydrogel, a carbohydrate, an inorganic bioactive compound such as a bioactive glass or calcium phosphate crystals.

27. The process according to claim 23, wherein the polymeric fibers of the first layer, second layer and third layer are each formed from a biocompatible and biodegradable polymer, optionally selected from the group consisting of poly(caprolactone), poly(lactic acid), poly(glycolic acid), poly(2-hydroxyethyl methacrylate), polydioxanone, poly(3-hydroxybutyrate), poly(3-hydroxyvalerate), poly(valcrolactone), poly(tartronic acid), poly(β-malonic acid), poly(propylene fumarate), polyanhydrides, tyrosine-derived polycarbonates, polyorthoesters, olyphosphazenes, poly(glutamic acid), collagen, hyaluronic acid, fibrin, alginate, laminin, elastin, chitosan, silk, keratin, cellulose, collagen and a copolymer or mixture of any of the polymers mentioned above.

28. The process according to claim 23, wherein the first, second and third layers are electrospun onto a rotating collector and wherein the collection speed for the first layer is at least 1000rpm and the collection speed for the second and third layers is from 10-500 rpm.

29. The process according to claim 23, wherein the process is a sequential process comprising sequentially electrospinning the first, second and third layers onto the same rotating collector to produce a layered construct.

30. The process according to claim 23, wherein the process comprises separately electrospinning each of the first, second and third layers separately and then laminating the layers together with a hydrogel to form a layered construct.

31. The process according to claim 23, wherein the process further comprises the step of functionalizing the layered construct by exposure of the layered construct to a protein or peptide.

32. A layered construct as produced by the process of claim 23.

33. A method of repairing, replacing or promoting regeneration of cartilage or cartilage-like tissue, the method comprising implanting the layered construct as defined in claim 1 into an implantation site in a subject in need of repair, replacement or regeneration of cartilage or cartilage-like tissue.

* * * * *